(12) United States Patent
De Joode et al.

(10) Patent No.: US 10,889,829 B2
(45) Date of Patent: Jan. 12, 2021

(54) COPY NUMBER VARIANT LEADING TO VIRUS RESISTANCE

(71) Applicant: RIJK ZWAAN ZAADTEELT EN ZAADHANDEL B.V., De Lier (NL)

(72) Inventors: Jasper De Joode, De Lier (NL); Raoul Jacobus Johannes Maria Frijters, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/924,473

(22) Filed: Mar. 19, 2018

(65) Prior Publication Data

US 2018/0223307 A1    Aug. 9, 2018

Related U.S. Application Data

(63) Continuation-in-part of application No. PCT/EP2016/059297, filed on Apr. 26, 2016.

(30) Foreign Application Priority Data

Oct. 2, 2015 (NL) ..................... 2015547

(51) Int. Cl.
| | |
|---|---|
| C12N 15/82 | (2006.01) |
| C12N 9/12 | (2006.01) |
| C12Q 1/6895 | (2018.01) |
| A01H 5/08 | (2018.01) |

(52) U.S. Cl.
CPC .......... C12N 15/8283 (2013.01); *A01H 5/08* (2013.01); C12N 9/127 (2013.01); *C12Q 1/6895* (2013.01); C12Y 207/07048 (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,779,241 B2 | 7/2014 | Mazereeuw et al. |
| 2012/0137388 A1 | 5/2012 | Mazereeuw et al. |

FOREIGN PATENT DOCUMENTS

| | | |
|---|---|---|
| WO | 2011/003440 | 1/2011 |

OTHER PUBLICATIONS

International Search Report and Written Opinion of the International Searching Authority dated Aug. 8, 2016, which issued during prosecution of International Application No. PCT/EP2016/059297.
Database EMBL "Cucumis sativus RNA-dependent RNA polymerase 1a mRNA, complete cds" Retrieved from EBI Accession No. HQ738485, Jan. 31, 2011.
Database EMBL "Cucumis sativus RNA-dependent RNA polymerase 1b mRNA, complete cds" Retrieved from EBI Accession No. HQ738486, Jan. 31, 2011.
Liebman, et al. "The Role of Cucumis SPP RNA-Dependent RNA Polymerase Genese in Antiviral Defense" XVI International Conference on Plant-Microbe Interactions, 2014.
Pico, et al. "Screening Cucumis sativus landraces for resistance to cucumber vein yellowing virus" Plant Breeding, 2003, 122:426-430.

*Primary Examiner* — Elizabeth F McElwain
(74) *Attorney, Agent, or Firm* — Duane Morris LLP; Thomas J. Kowalski; Deborah L. Lu

(57) ABSTRACT

The present invention relates to a genetic determinant which may comprise at least two copies of a combination of two closely linked RDR1 genes, which two closely linked RDR1 genes are inversely oriented, and which genetic determinant leads to virus resistance when present in a plant. In one embodiment, of the RDR1 genes in the combination is represented by SEQ ID No. 1 or has at least 70% sequence identity, and one of the RDR1 genes in the combination is represented by SEQ ID No. 3 or has at least 70% sequence identity; or one of the RDR1 genes in the combination encodes a protein represented by SEQ ID No. 2 or a protein that has at least 70% sequence identity, and one of the RDR1 genes encodes a protein represented by SEQ ID No. 4 or a protein that has at least 70% sequence identity.

18 Claims, 13 Drawing Sheets
(5 of 13 Drawing Sheet(s) Filed in Color)
Specification includes a Sequence Listing.

Fig. 1A

Genomic sequences SEQ ID Nos. 1, 3, and 5

**SEQ ID No. 1 - *CsRDR1_II***
>Cucumis sativus_cs9930v2_emv_14138_genomic_sequence

```
AATACTACAACAATAATTCTTCTCCCAAACACATACTATCATAATCCTTCCTCCAAACAC
ATACAATCATAACACTACCATTCATATTCCTTCCCCAAATAACACATATTACCATAACA
CTACCAATAATAACCCAAACCTTAAACACATATTATCATAACACCAAGATTATTATAACA
CTAGGATTGCCATAATCTTTCCCTCCCCAAATGCACCCTAAGAATTTTGCCATATTTGCA
AAATTATAAATCAATGTGCTATATTTGTGATAACATGTTCTCAAAATGCTACCTACTACA
ACTTTTCAATAAATAAGTAGAGACTAACTAGAGCAAGGTCAGGACAGGGAGTGTCTTCAT
CTTGGTTTAGCTCACAGTGAGTTTTAATTTTTTTTTTTNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNCTTCCACTCCCTCTCCATTCTCCACGTGGTTCAGTGCAGGT
CTCGGGCACCCGTCTCACTGGAAAAATTGGACATGTCTAGAAATATTTAAAGCATATCTC
AAAGTTTACGGTCATTGGTATTCTCTCTATGAAGACCTTCAAAATATTATTTAACACGGT
CACAATTAAATATTTGAGAGAGAAACAACGTAAGTATTTCAAAATATGTATCAATAAATT
TTGTAGGTATTTCCATATTTATGTAGATTATTGTGAATCAACCTTTGTATCATATGATTA
AAAATATATATATGAAACAACAAAATGTACTAATATGTAAATCTAATATAATATAAACAA
TATGGTATATTTTCTATTGATTCCTTTAATAAGAAAATGTTTTCTATAATTTTTTTTAAA
AAAATATCAATCCACATAGAAAATTCATATCCATTGGCGGCTCATTCAATAATTTAATAT
ATTCTTTTCGAAAACTAGAAGCCAAAATTAAAAAAAAAAAGAAATTACATTCAATAGAGA
ATATTTGGTGTTATGGCCATGGAAAGCTCAAAAAGAAAGACCTGTCAATGAAAGTCTTTC
TTTACTCTTAAGCTAAAGGCCCCCAATTATGGAATTATATCTCTTCATTCCTCCATTTTC
GTTTCTCCATTCCCCAACTCTCCTATTTTGCACTACACTGTTCTCTACTGCCTTCTGCAT
CCTCTTTTCATGAATCAATCTGCTTGGTATTCACCTAACTTTTTCTTCCATTGTTGAGAA
TAGATGGACTATTGATGTGTTTTTCTTTTTATATTGTAAAGCTATTCTTCTTTCTTTGTG
TTTCTTCATCTGGGTTCATTTTTTATCATGTTTTTTCCCATTTCTTTTTGTTCCCCTGTA
TTTTCTTTGTATTTAGCAACGTATCCTCTTCTGCTCTCTCTGTAGATTCTTACTGCTTCT
GGGGCTGTTTATGATCTGGGGTTGTTTCTTGTCTTCAAATTTTAGTTTTCACTATGTGGG
TGTCCGTTTGATTATGAAAACGTGTTATTCTGATGTTCCCACACATTTTCTTGATCATGT
ATGAGTTACCATTAGTATGCATTCTGCTCTTTACCAAATGAGTATAATGTGATCTAGCTT
TCTCTATTAATGTCGGTGAGATCCTCTATATCTTGAATGTGTCATACCTTTTCAATTTGA
TCAAGATGATAATGTTTTTGCATTTGGAATGAAGTTATATATAGAAACTTATGGAAAAAG
GGTTAAATAAATATTAATCTTTCCTCGATGGAATGTAAGAAACACTTTTTAATCTATCTG
CTCACTTCTTTATTTTGAGACTTGGTTTTTTGGGTTGAATAATATATGGGGTGAGGTATT
TGAACAGTTGATCTTTTGGTCAAGGGTACATATATTATGCTAGTTGAACTTGGCTTTCTT
TTTAGGCTTCATCATATGCATTGTAATCAATTTGTTTGATATGACAGAAGAAGTTCGGA
GTTGATTTTCTTGGATTGGATGGGTAAAACAATTCAGCTTTTTGGATTCCCTTCTGGTG
TATTGCAAGAATCAGTTAAGACGTTTGTAGAGGGAATTACAGGCACAGGAACTATTGATG
CCATAAATACGAAACGTTCGAAGGGAGGAGGAAGACGAGTGTATGCTATCATCCAGTTTA
CTGATGAAGAAGGTGCTAAGTCAATTATATCTAAGGCTACTGAACGCCTTTGTTATGGTA
CTTCTTATCTGAAGGCAAGGGAGATGAAACATGATATTCTACCAGATCCGCTTGTCTTTG
ATTACAACTTCAAAGCTCTAAGACTACATCTTGGCTGTCAGATATCAAAGGAAAGTTTTT
CCGTGTTATGGACAGAGTCGAATGTTTCTGTAGATTTCGGGTTTGAGCTGCGCAAGCTTT
ATTTCTTCATATCCTATCCTCGTGTTGACTACATGCTCGTATTGCGCTACGAGAACATTT
GGCAGGTTGAGTTACACAAGCCACATGGTCAATCTGTAGATTATCTTCTGATTCAGGTTC
ATCCATTAACTTTGAACAATGTCATGTCATTAGTGTACTGTTGTATTTTCTCCTCACTAT
TGAGAAATATCATTGATTCATCCCAAGCAAGTTTCACCTAAATTTTTCACTTTATTCATG
GTATTGTTCTCTAATTACGGGGATTCAACTACTGACTCATGTACGTGCTCATAGGCCTGA
TTTCCATCACAGAACAGTGGACGGATATAAAATGATAACTGAAAATAAAAATTTAGTGAA
CCACTAAAATCATCATTTATACCTAAGTTCCTGAGAGAAATATATAGACTGAACACTTTA
TGGGACAAAGGAATTAAGTGAATTTATTGATAACTTCGATGCAAAAAGAACTGAGAAAC
GATCAAGGTTTTATCAAAAGATTGTAAAAGGGATAGTGGAAGATAGCTGTAGATAAATTC
CAGTGCTTCAAATGGGTGAAAGAAGCTATAATTTTATTAAAAAGGTGTCTTAGTTGATAA
```

Fig. 1B

```
TTTTATCATACATTTTTTCTCCAACTTGATAACTTCAAGACTATGGGTAGGATTTGGATA
TAATGAGATTTTGAGCCATATAAGGTTAATGTTGTTTAGTAATTGTAATCTGGCAGGATA
TGTTTTCTTTGAACAGAGCTAAAACATGTCCCTAGATATGAATTTTAACAAGCTAAGTAT
AAACAGAACTAAGCTTGCAACTTTTCTATATTTCTATACTTCAGGATAAGCTTATAAACG
CAGGTAATCCGTGCAAGTGAACATATGTTTCATAAAAACAAATTATGCTGTCTTCATACT
GATGTTGAAATAAGCAAGTCAAAGTTCAATGGCAAGAATTTGAGAATAGCTTAGGTTCT
TGGCCCATGCACATTTTATGTTGTATATATTCTAACTATGACATGTTTGTACTGTTAGTT
ATTTGGTGCTCCACGGATTTATGAAAGAGATGCAAGGTCTTTTGGACTCATTACTGAAGA
CCCTTTCTTAAACTTTTCCACGGAAATTGACACCCAATGGTTTCGAGCAACTGATTTTAC
TCCATCATGTAGTATTGGACAATCTGCTGCTTTATGCTTGGAGATTCCCTACGGTCGCCA
GCTCCCTAATTTTCATGATAAATTTGCTTACTTCAAAGAAATCAAGGGTAAATTTACATT
GGTCAGTGGTTCTACTTATTCCTCCAATGTAAACTTGGTACCTGTAGTTACACCTCCTCG
AACCATCAACTTGCCATATACAATTTTGTTTAAGATAAATTTGTTGGTACAACAAGGATG
TCTTCCAGGCCCAGCTCTTGATATTAGTTTCTATCAGATGGTAGATTCTCAGATATACAA
TACTGCCGTCATAGATCATGCGTTAAAGAAACTTCTCCACTTGAAAGAGTGTTGCTATAA
CCCTTCAAAATGGTTAGATGAGGAATACAGAAAGTACTTCAAATTAAAGAATCCCCCCCA
GCCACCTATTTTGACCTTGAATGAAGGGTTAGTCTATGTACACAGGGTTCAAGTGACACC
TTGTAAAGTTTACTTTTGTGGTCCAGAAGTTAACATTTCAAATCGTGTATTACGCCGGTA
TCCTGACTACATTGACAACTTTTTGCGTGTTTCATTTGTTGACGAGGAATTGGGTAAAAT
GTATTCAACTGAGTTGTCTCCACGTGCATCTTCTTCTTTGGAGGATGGAAAGACAAAAAT
TTTTAAACGGATTCTTTCAGTTCTAAGAGATGGCATCACTATTGGTGATAAGAAGTTTGA
GTTTCTAGCTTATTCATCTAGTCAATTACGGGAAAATGCTGCATGGATGTTTGCTCCAAA
AAATGAACTTACTGCAGCTAAAATAAGGCAATGGATGGGAGATTTTCATAATATACGAAA
TGTAGCCAAGTATGCTGCTAGACTAGGCCAATCCTTTGGTTCATCAACAGAAACTTTAAG
TGTCAGTAGACGTGAAGTTAAAGTTATTCCTGATATTGAAGTTGAATCAGGTAGTGGTGT
CAATTATGTCTTCTCTGATGGTATTGGGAAAATAGCAGCTAGTTTTGCTAGAAAAGTGGC
TAAAAAATGTGGGATCAGGCATACACCATCTGCTTTTCAGATTCGTTATGCTGGTTTTAA
AGGTGTTATTTCTGTTGATCCTACCTCATCAGTAAAATTATCGCTAAGGAACAGCATGCT
CAAGTATGAATCAACAGACACGAAGCTTGATGTTTATCATGGAGTAAATATCATCCTTG
CTTTCTAAATCGTCAGTTGATTACTCTTTTGTCTACACTTGGAGTTCAGGATCATGTTTT
TGAGAGTAAACAACAGGAGTTGATTGATGAATTGGACACCATTTTAGTGATCCATTGAA
GGCTCAGCAGGCTCTTGAGCTAATGTCTCCAGGAGAGAATACCAAGATACTTAAGGAAAT
GATGTTGTGCGGTTACAAACCTGATTCTGAACCTTTCTTAAGAATGATGTTGCACACATT
CAGAGAATCAAAGTTGATGGAATTGCGAATGAAGTCAAGGATCTTCATTCCAAATGGAAG
AGCAATGATGGGATGTCTCGACGAAACAAGAAACTTGGAATATGGGGAGGTATTTGTGCA
GTGTTCTGCACATCAGCAGCTGCATGACGATCGCGTAATCTTTAAGAGAATAAAATCGAA
CCGGCATTTCATTGTAACTGGAACAGTTGTAGTGGCCAAAAACCCCTGCTTGCACCCAGG
TGATGTGCGCGTTTTAACAGCCGTGGATGTACCATCACTGCATCACATGATAGATTGTGT
GGTTTTTCCACAAAAGGGTCAAGGTAAATGATCTATTTTAACATCAAAATTTACATGTC
CAGTTCAAGTAAAATAAAATATATTTCTCCTTTTCAGTCTTAGATATATGTTTATACTCG
ACTTAATGAATTCTTAACTGTGTGGCTAAGCATCTCTAATGTCATCATGTTTACTAGTAA
TTTTGCTTATCTTAGAAACTTCTTTTTTTTTACTTGCCTTGAGGGGTGTCATAACTCTAA
TTGATCTTACCTACCTTTATTCTCTATATTTCGTACTTTCTTCCTTCTCAAGTTGATAAA
ACCGTTTCTCTTCATGCCTCTAGATAGCCAACACATCATCAGTGAACTAAAGTAAAACTA
TGTGTTGTTTTCTTCTCTGCCTGCTGATTGTTTTTGTCATAGCACTTGTCTTGTTTGATT
CTTGCATGTTGATTGTTTCTGTCATAACACTTCTCTTTCTATGTAAGACCTCATCCAAAT
GAATGCTCTGGAAGCGATCTAGATGGTGATATTTACTTCGTCTGTTGGGACCCTGATTTG
ATTCCACCTCAACAAGTTGAACCAATGGATTATACCCTGTACCTAGCCAAGTACTAGAT
CATGATGTCACAATGGAGGTATGGTTTACAAGTGAACTTTGAACTGTTGTTATCATCAAC
AAGTATTTTAGAGGAAAAGGTTGTTCTATAGTGTAAATGTTGTAATGCAGGAGGTCCAG
GAGTATTTTGCAAATTATATGGTCAATGACAGTTTAGGAATCATTGCCAATGCTCATACA
GCTTTTGCAGATAAAGAGCCAAAGAAAGCAATGAGCAATCCTTGTATACAGCTCGCAAAA
CTATTCTCAATTGCAGTCGACTTTCCGAAAACTGGAGTCCCTGCTTTAATACCTGCTAAT
CTAAGAGTAAAAGAATATCCGGATTTCATGGATAAAGCCGACAAAGTGACATACGAGTCG
```

Fig. 1C

```
GAGAATGTACTGGGGAAACTATTTAGAATGTTGGATAGCATTGGTCCAAACATTAAGAAT
ATCAGGTCCTTCAACTATACGCCGGAGATGGCTCGGCAAGATTATGACCCTGACATGGAA
GTTGAAGGTTTCGAGGAGTACCTCGACGATGCAATATATCACAAGAACAACTATGACATG
AGGTTGGGAAATTTGATGCACTATCATAAGATCAAAACTGAGGCGGAATTGATCAGTGGT
GGTAGTTTGACGTCATCATTATCTTTCACCATGAAAAATGAAGCGGAATCGATTATCTTG
GCTGTGAAGTCGCTGCGAAAGGAGGCGAGGGGCTGGTTCAATGAGAAAGCAGACTTACAT
TATGGACATCATACTAATGTGTATGCAAGAGCTTCAGCATGGTATTTTGTTACATATCAT
CACACCTACTGGGGGTGGTCTGATGGCAGAAAGAATCATGGCCATTTTCTTAGCTTTCCA
TGGTGTGTTTATGATAAACTCATCCGTATCAAGCACCGCAAAATTAATTGTAGAGCTCGC
TATTGA
```

**SEQ ID No. 3 - *CsRDR1_I***
>Cucumis sativus_cs9930v2_emv_14137_genomic_sequence

```
TTAAATCACGTTTTTAAAAATGAAAACTACCATATCAAGCATTAGTATGGTCAATAAGTGGGTGTTTGTTGAA
CTATAATAAAGTATGATTGTAATATAATATAATCTAAAATCCATGTTTGGATACCGTATTTGCGTTCAAATTG
CAATATCGAACTTATTTTGTTTATGCAAATTTTAGTTTAATATTGTTTAGAATAGTTGTAAATATAACAAATA
AATTTAAAATAATTAAGAATATAACAACATTTTTAAAAAATTGCAAATATAACAAAATCTGTAAAAGTCTATC
AATAATAGATTATGTTGCAAATATTGGTCTATCACTAATAAATCATAAGAGTCTAGTGTAGACTTTGCAATAT
TTACAATGTTTTTAAAATGCTGTTATATACTTAATTATTATTTCTAAAACTGTTATCCATTATAATTACTCAT
CTAGTTTCTTTTTCATCGTTTTCACGGTTCAAGATCCTATTTTTATTTGGTTCTCAATCGTTGTGCATTCCAG
CACTCCTCTTGTTACCAATAATCTATTTTGGCTTTCCAAACAACCGATAAGGATCAATGTAAATAGTTAAAAG
ACTTAGATAAATAGATTCAAGTTAGTGTTGTGTTTATTTGAGTTTCTCAACAAAATATTGAATAGTTACTGTA
GTTAGTTGGGCACTCTTAGTCTTATATCTTGAAAATATAAGAAAATTACGTGGTTTTGAGAGAAATATTGCAT
ATTTTTTATTATTGAATATGACCCAATAATAGGTAAAAATACTACCGAAGAAATTCTATCCAAGGTAACTTAT
GGTTCCTTTGGATTAGCTTTAACTACAAGTCTTGGTAAAAATGAATGAGTTTCTCTTGTACCTCTTTAAAAAC
AACAACGTAACACAAAATATACTGCTAAACATAAAAGTAAAGTCAAAGATGAATATGACGAGAGTTATAACAA
TTAATATTATAGAATAAAAATTATTATATGAAATGAAAAACACATACCTTTCTCAAAGAAGGAAAAACACATC
CAACGAGTAAAAAGAATAAAAGTAACCTAAATGGAGGAAAAATTAAAATGTTCGTAAAAACATGGTTGAAGGA
AAGTTTGAAAAGAAGATAAAATGTTACCAACTAAACTAATGTGTTAGGAAAGAAGTAAGAATTTGAAAAGATA
ATGAAGCAAATTAATTATAAAATAATGTAATTAATAAATTCCTTTTACAAAAGTCTACTTAGTTATTTACTTT
TAATATAAACAATATGTAATGCTTATTTGGCAAAGAATAATAGAATTGAAGAGAAAAGGATTATTGTTGTAAA
TTAATGTGAATTGAATAATATATTTGAAAAGTGAGAATTCATATAATTGGTTTGTGTTTTATTAAGAAATA
GAAAAAGAGAAAATAATTGTACTAGAAAGGTTAAACTTAGGTAGCAAGTTTTGTTTGTGATTTTCCCATCTGG
CGTCAAGTCAAGGCTTTTGGGAAATGAAGTCTATTATTAAAGCTTTCAAGTTCTTCTCATGCCCCACAAAAAC
ATTTTTAAGAATATTACTTTACTTGAAATTAATTATTTTTACTTATTCTTACTTTTCAGTACGCTTTATCTTT
AATGTAATCATATAATAGAAACACACTAAAATTTAATTAGCATCAATAAGTAAATTTGAAAATCAAGGAAACA
TAAAACCTAAAATAAAGGGAACCCCATGTTGAAATTTTGTGCATTAAATAGCAAAAATTTGACTTTTGATCCA
CAGCCTTATTTGGTGAATTACTCCATGATGTTTTGATTTTGATTTAGACCATATTGGTAAAACATATTCTAAG
TCCTTCTTTTAGCTCTCCCACAACGTCCCCTTATTTATGGATGTTCATTATTTCAGTCATAGTGTGCCAACTT
CTTTCGGTCACTAGGTCTATCCGTAGAAGATAAAGTTTCAACCGATCATTTAAAGAAAACGAGTAGATATTGT
TATAGATTAAAATCAAAAAGATTGATGAAATTGGATTGGAATCTATATTTTGTTGATTGATTTTGTCAACAA
ATTAATCTATATTTATATGAGTGAGATGAAAGGAAATGAAGAATTAAAGAAAAAGACATTGGAGATATTTTAA
ATTTATTAAGGTATGTTCATATATTTGGGTTGGATTTGGTTTGGGGATGGATTTTCAGACAAAGATCAAACAA
ATTAAAAAATGGTTGATTTTCTCCAAATTCAATCCAATTCATTGGGTAAGTTTGGTTTGATTTGGTTTTACCC
ATTTTGAAACCACAAGGACTAAATATGATCCATCAAATTTGGTGACAGAAATATGTTTTTGTATTAAAAATGG
TGATTTCACAAGAAAAAACCAAGAAAAATAGAGCAAGATGAAAAGGTTAACCAAAGGGTGCTATTTCTTTTTG
ACAATTTGACTGGTTACACCTCACTTGATCAGTCTCTACTTCACGATCCCTCGTCTCCCTCTGTATGGGCTCT
CAAACGGTCAGACCAAAAGTTACGTTGGAATTACTGGCGCTGAAGCGATTTCTTCTTTCAAAGCTCCAACAG
TATGTTCTGTTCATCACTCCTTCTCCTTTTGCTTTCCTTTTCTTCTGGGTTTATGGCCTTTTGATGTTGCTTC
AGTTTTTGACATTCCATTAAACCTCTTCTTGTAATTACCAACTAACTGGGGACTGGGCTTGCTGCTCTTGCAG
TTGACTCTTCGCATTCCTCTGTTTTTACTCTGTTTTTACACTGTTTTTTGGTTTTGATTGCTCTACTGGGTTC
ATATGGAAACTTCAAAATCCTAAAGTTTTCATTTCGGTTTATCGATTTGTGCCACTTGGAGGGGATTTTTCAT
```

Fig. 1D

```
GTTTTTTTTTTTTTAACTGTGGGTTTCTCTGTGTTTCTTCTGCTCATATCTTTTGTGCCTTTTAATTGTCTT
TTCTTCCCAAATTCCCTTCAAGATCCTCAGGTTTTTGTACCCAGTGGAGGACATTTATGTTTTTATGTGTGT
CGTTGGACCTTTTTCTTCTTCATCATTACATCATGCTATTTTTCTCATTTTCTTGGCGCTTTTGAATTTCTT
TTCTTGAATTTTTTTTAGTTGGAGTTTGATCTAGGCGAGCACTCAGGTTGGAAACTCGAGCATTCACCTATAT
TCTGGGGCTGTCTGATTGTGTGTCTCTTTCCATTTTCAAAACAAAGGTTTCTTTGGTTTCTTTTCATTGAGTG
TTTCTTGTCGAGTAGGTTACTCTTCTTTTCTTCATTTCATTTAACTTATCTGCATCTGAATTGTCACTGATTC
TAATTCAATCCATGTATTGGTATTTGTTTCTCTTCGTAGGACAACATTCACCCTTGGCAGTTTCATTAACTAG
ACCTTATTTTCTTCACATTGTCATGGAATGCTCCATTCAAATTGGAACCCCAATACGCATAGGAGCATAGAAG
TTAGGCCTCTTAGAAAGTCGTGAAAGATTTCTTTGGAATCTCATGGGGAAAACAATTCACATTAGTGGATTTC
CTTCACATGTCACCGCAGATGCTGTTAAGAATTTTTTGGAGGGTCATACAGGTCCAGGTACTGTGTATGCCAT
AAAGGTTAGACCACCTAAGAGAGGGGGAGGTAGACTATATGCTATTGTTCAATTCACTAGTGCTACACAAGCT
GAGTTGATCATTTCTTTAGCTAATCAACGTCTATGGTACGGATCTTCTTATCTTAAGGCTCGGGCAACCGAGG
TTGATATTGTACCAAAACCTAGGACATACATGTATACCTTGGAAGAGTTGCTGCTATGCTTTGGTTGTCAAGT
CTCAACTGAAAAGTTTCGTGTTCTATGGAAGGAAATGTTGATTTGGTGACTTTTGGAATTGGAATGCGGAAA
ATGAACTTTCATTTGAAATATAAGTCTGTTGAGTATAGGCTTGAGCTTTCATATGAGATCATTTGGCAGATAC
AACTGCACTGTCCGCGAGATCAGTCTATGAAGTATCTTCTGATCCAGGTTCTATGATCAAATGTCTATCTAAA
TTTGTTTCATTTTATTTTGAAAAGCATAATTATCCTCTCTTGTAAAGTTGAAACATTTTGCTATACTTGTTTA
AATTGTTTCAACTATTGTGTTAGTTGTTTGAACATTAAATCGATGTAACCTTGTTGAAAATGTTGCTATTTGT
CTTAAATAGTAGATATGTTACTCACATGTAAGCTTAATAGTCAGGTTATCTTTTCATGTTTTTCTTATCAGT
TAAGTGGAGCTCCTCGGATATATAAAAAAGTTGCACCGAATAGTGGACAAATCTTCGACAATCCACTTTTGAA
CTTTTTTAAGGAAGCATCTGATGATCAATGGGTTAGAACGACTGATTTTACTTCATCATGCTCTATTGGACAA
TCTTCTTCTTTATGTTTGAAGCTACCTAATGGCCGTCAACTTCCACCTTTTAAACAAAATTTGCTTATTATG
AAGAATTTGAACATGAATTCCGCTTGATAGATGAAGATGCCAATTTTTCTTTTTGTAGAGATCTTGCTCCCAT
TGTTGATTCTCGTTCTCATGTTCTGCCGTATAAAATTTTGTTTAAAATAAATGCATTAGTTCAATATGGTTGC
ATTCCATGGCCATTACTTGATGCTAGTTTCTACCGGTTGGTCGAAAGAATAATAACAACAAGAATTGAATTTG
TTGAACATGCCTTGGAAAAACTGTTCCATTTAAAGGAATGCAACTATGATCCATCAAACTTTCTTACAGAGCA
GTACAGAAAGTATTCAAGACATCCTCCAAATTCTCCTGTTATATCCTTGGATGATGGTTTGGTATATGTTCGT
AGGGTTCAAATAACACCTTGTAAGGTGTTCTTCTGTGGTCCTGAAGTCAATGTCTCAAATCGGGTGTTGCGCC
ATTTTTCTCAATATATTGATAATTTTCTTCGTGTGTCTTTTGTTGATGAGGAGTGGGATAAAATGCGTTCAAC
AGATTTATTGCCACGGATGTCTTCAAAGAGTGAGGATGGTAAAACTGATATCTACAGGAGAATTCTCTCTGTT
CTTAAAAATGGCATAGTCATAGGTGATAAAACCTTTCAGTTTCTTGCATTCTCATCAAGCCAATTAAGAGATA
ATTCCTTGTGGATGTTTGCTTCCGGACCTGATATTGACGCAGCTTATATTAGAGCGTGGATGGGCGATTTTCG
ACATATCAAGAATCCCGCAAAGTATGCTGCTAGATTGGGCCAATCATTCGGCTCATCGACAGAGGCACTTTCA
GTTGCTAGTAATGAAAGGGAAATTATTCCTGACATAGAGGTTCAACAGGGAGAAATCAAGTATGTCTTTTCTG
ATGGAATTGGAAAAATATCAAGCAAATTCGCCAAAGAGGTTGCTGCAAAATGTGGTTTCCAAGCCGTCCCGTC
TGCTTTTCAAATTCGTTATGGTGGATATAAGGGTGTTGTTGCTGTTGATCCGTACTCAACTATAAAATTATCT
CTGAGGAAGAGTATGTGCAAATTTGAATCAGACAACACAAAACTTGACGTCTTAGGCCATAGCAAATACCAAC
CATGCTTCCTTAATCGTCAACTGATTACTCTCATGTCTACTCTAGGTGTTAGAGACGAAATTTTTGAGAAAAA
ACAAAGTGAAGCTGTAGAACAATTGGATGCCATTTTAACAGATCCATTGAAGGCTCAAGAAGCTTTGGAGTTG
ATGTCTCCCGGAGAGAATACTAATATTCTCAAGGAAATGCTCAAATGTGGCTATCAACCAGATGTCGAGCCGT
ATCTGTCAATGATGTTACAAACTTTCCGGGCATCAAAGTTGCTAGAGTTACGCACCAAATCAAGAATCTTTAT
CCCAAATGGGAGAGCGATGATGGGATGTCTTGATGAGACCAGGACCTTGGAATATGGGCAGGTATTTGTGCAA
ATCTCCAGTGGTAGACATCGAAATTTATCTGAATCCTTCGCATTCAATAGAATTGGTCGAGAACACCATTTAG
TTATTGAAGGAAATGTTACAGTTGCTAAAAATCCCTGCCTGCACCCTGGTGATGTTCGTGTATTAAAGGCTGT
AAATATACCTGGTTTGTACCATATGGTTGACTGTGTAGTTTTTCCTCAAAAAGGATCAAGGTTGGTAGTACAT
TGACCAATGCTAGTTCTTTCTTGATTTGGACAATAAGTTATGTTTTCAAATTTAAATGCAAGAAAGCCCCTTC
ACTTCAGAATAGTAACATGTCAACATATATTTTCTAGAATAGGTTCTGTGACTAATAGCTTGCATAATTTTGG
TTGGAAGATTTTCCTCTTAAATAGATGTTACTAACCAGATTTTGTACTTGTTTATTTAGGCCTCATCCGAATG
AATGCTCAGGTAGTGATTTAGATGGTGATATTTACTTTGTCTGTTGGGACACCGAATTGATCCCGTCTCGACA
AATTCCACCTATGGATTATACTCCTGCACCTCCAAATGAGTTAGATCGTGATGTTACAACTGAGGTATTTTGA
CAGTGGCATGTTTTGAAAACTTGATAACTCATGCCACTTTTTCAGTGTTTAATCTCCGTTTTAATATTTGACA
TAACAGTGAACTTCAATTTATGTTTTTTTCTTAAAATAGATTCACGTTGCGCATTGCTTCTCATTAGAAGAG
AGACCATTCATGTTTGTATGTGTTCTTAGTCCTAATCTGAAACTACTGTTCTTTACCACAGGATATCCAAGAA
TATTTTGTGAACTACATGGTTAATGATAGTCTTGGAATCATTGCCAATGCTCATACTGCCTTTGCAGATAAAG
AGCTCTTTAAAGCAAGGAGTAGTCCTTGTTTGGAGCTTGCAAAGCTATTCTCCGTTGCTGTGGACTTCCCAAA
```

Fig. 1E

```
AACTGGAGTACCAGCTATAATACCTTCTCATTTATATGTCAAAGAGTTTCCTGACTTTATGGAGAAGCCTGAC
CGACCCTCTTATGAATCAAACAAAGTAATTGGAAAACTTTTTCGGGCTGTGAAAGACATTGCACCAACTTTAA
GCCATATTCGGTCATTTACTCGAGATGTAGCAAGAAGGTGTTACGACTGTGATATGGAAGTCGAAGGCTTTGA
AGATTATGTTGAAGATGCCTTCTATCATAAAAGCAATTATGATTACAAGTTGGGGAATTTGCTTGATTATTAT
GGTATCAAGTCTGAGGCAGAAGTACTTAGTGGGAGTATCATGAGGATGTCCAAGTCTTTCACCAGGAGAAGAG
ATGCAGAAGCAATCAACTTGGCTGTAAGGTCTCTGAGAAAGGAGGCTAGGACATGGTTCAATGCAAGAGAAGG
CGCAGATTCGAATTCAGATGATTTATTTGCCAAAGCTTCAGCTTGGTACTATGTTACATACCATCACTCTTAT
TGGGGCTGCTATAATGAGGGAATGAAACGCGACCATTATTTGAGCTTCCCCTGGTGTGTTTACGACAAACTGA
TGCAAATCAAGGAGAATAATTTGAGAAGAAGAGAGAGAGCTGCAAGACTGGCAAGTTTCGACAGATTCGGACA
TGTGTTAAATCTTGGTGGGAGTTGAAGAATGATCAATATGGTTGGTTTGCTGTCAGATTGAACTAAATTTTTC
TGTAGCTTTAAATGATTGAACTAAGAGAGGAAACTTGAAATGGAAATTGTCTTTTAACTCGTTGAAAACTTGT
TAGTTTATAAGGAATGTTGTTTCTGTTTACCGTGTAATATCCACATTCGCATGTACAGAGTTCATGAAATCTC
AAACCTTAGTCTCACTTTCTCTTAAACTATAGCCCATCCTCCTGCCAGCTTTTTATGTGCGTACTCGTTGATT
TATGAGATCATCTAGTGGGGAATCTCCATCTCGATTCCTATAAAATTTAACAAATTTTTTTTGTCAAAATGA
ATAGTTAAACAAAAGCAAGGATGATGAAGCCTACTTTGTCTCCTACCCTGCTCTCTAAACATCTCTATGTATC
AATGGTCAACACCAGGATTATCAGATATATCATATGTTACAAGA
```

**SEQ ID No. 5 – *CsRDR1_II* modified with indel (CAGGT – bold)**
>Cucumis sativus_ 14138 modified_genomic_sequence

```
AATACTACAACAATAATTCTTCTCCCAAACACATACTATCATAATCCTTCCTCCAAACACATACAATCATAAC
ACTACCATTCATATTCCTTCCCCCAAATAACACATATTACCATAACACTACCAATAATAACCCAAACCTTAAA
CACATATTATCATAACACCAAGATTATTATAACACTAGGATTGCCATAATCTTTCCCTCCCCAAATGCACCCT
AAGAATTTTGCCATATTTGCAAAATTATAAATCAATGTGCTATATTTGTGATAACATGTTCTCAAAATGCTAC
CTACTACAACTTTTCAATAAATAAGTAGAGACTAACTAGAGCAAGGTCAGGACAGGGAGTGTCTTCATCTTGG
TTTAGCTCACAGTGAGTTTTAATTTTTTTTTTTNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNCTTCCACTCCCT
CTCCATTCTCCACGTGGTTCAGTGCAGGTCTCGGGCACCCGTCTCACTGGAAAAATTGGACATGTCTAGAAAT
ATTTAAAGCATATCTCAAAGTTTACGGTCATTGGTATTCTCTCTATGAAGACCTTCAAAATATTATTTAACAC
GGTCACAATTAAATATTTGAGAGAGAAACAACGTAAGTATTTCAAAATATGTATCAATAAATTTTGTAGGTAT
TTCCATATTTATGTAGATTATTGTGAATCAACCTTTGTATCATATGATTAAAAATATATATATGAAACAACAA
AATGTACTAATATGTAAATCTAATATAATATAAACAATATGGTATATTTTCTATTGATTCCTTTAATAAGAAA
ATGTTTTCTATAATTTTTTTAAAAAAATATCAATCCACATAGAAAATTCATATCCATTGGCGGCTCATTCAA
TAATTTAATATATTCTTTTCGAAAACTAGAAGCCAAAATTAAAAAAAAAAACAGGTCTCAAAAGAAAGACCT
GTCAATGAAAGTCTTTCTTTACTCTTAAGCTAAAGGCCCCCAATTATGGAATTATATCTCTTCATTCCTCCAT
TTTCGTTTCTCCATTCCCCAACTCTCCTATTTTGCACTACACTGTTCTCTACTGCCTTCTGCATCCTCTTTTC
ATGAATCAATCTGCTTGGTATTCACCTAACTTTTTCTTCCATTGTTGAGAATAGATGGACTATTGATGTGTTT
TTCTTTTTATATTGTAAAGCTATTCTTCTTTCTTTGTGTTTCTTCATCTGGGTTCATTTTTTATCATGTTTTT
TCCCATTTCTTTTTGTTCCCCTGTATTTTCTTTGTATTTAGCAACGTATCCTCTTCTGCTCTCTCTGTAGATT
CTTACTGCTTCTGGGGCTGTTTATGATCTGGGGTTGTTTCTTGTCTTCAAATTTTAGTTTTCACTATGTGGGT
GTCCGTTTGATTATGAAAACGTGTTATTCTGATGTTCCCACACATTTTCTTGATCATGTATGAGTTACCATTA
GTATGCATTCTGCTCTTTACCAAATGAGTATAATGTGATCTAGCTTTCTCTATTAATGTCGGTGAGATCCTCT
ATATCTTGAATGTGTCATACCTTTTCAATTTGATCAAGATGATAATGTTTTGCATTTGGAATGAAGTTATAT
ATAGAAACTTATGGAAAAGGGTTAAATAAATATTAATCTTTCCTCGATGGAATGTAAGAAACACTTTTTAAT
CTATCTGCTCACTTCTTTATTTTGAGACTTGGTTTTTGGGTTGAATAATATATGGGGTGAGGTATTTGAACA
GTTGATCTTTTGGTCAAGGGTACATATATTATGCTAGTTGAACTTGGCTTTCTTTTAGGCTTCATCATATGC
ATTGTAATCAATTTGTTTGATATGACAGAAGAAGTTCGGAGTTGATTTTTCTTGGATTGGATGGGTAAAACA
ATTCAGCTTTTTGGATTCCCTTCTGGTGTATTGCAAGAATCAGTTAAGACGTTTGTAGAGGGAATTACAGGCA
CAGGAACTATTGATGCCATAAATACGAAACGTTCGAAGGGAGGAGGAAGACGAGTGTATGCTATCATCCAGTT
TACTGATGAAGAAGGTGCTAAGTCAATTATATCTAAGGCTACTGAACGCCTTTGTTATGGTACTTCTTATCTG
AAGGCAAGGGAGATGAAACATGATATTCTACCAGATCCGCTTGTCTTTGATTACAACTTCAAAGCTCTAAGAC
TACATCTTGGCTGTCAGATATCAAAGGAAAGTTTTTCCGTGTTATGGACAGAGTCGAATGTTTCTGTAGATTT
CGGGTTTGAGCTGCGCAAGCTTTATTTCTTCATATCCTATCCTCGTGTTGACTACATGCTCGTATTGCGCTAC
GAGAACATTTGGCAGGTTGAGTTACACAAGCCACATGGTCAATCTGTAGATTATCTTCTGATTCAGGTTCATC
```

Fig. 1F

```
CATTAACTTTGAACAATGTCATGTCATTAGTGTACTGTTGTATTTTCTCCTCACTATTGAGAAATATCATTGA
TTCATCCCAAGCAAGTTTCACCTAAATTTTTCACTTTATTCATGGTATTGTTCTCTAATTACGGGGATTCAAC
TACTGACTCATGTACGTGCTCATAGGCCTGATTTCCATCACAGAACAGTGGACGGATATAAAATGATAACTGA
AAATAAAAATTTAGTGAACCACTAAAATCATCATTTATACCTAAGTTCCTGAGAGAAATATATAGACTGAACA
CTTTATGGGACAAAGGAATTAAGTGAATTTATTGATAACTTCGATGCAAAAAGAACTGAGAAACGATCAAGG
TTTTATCAAAGATTGTAAAAGGGATAGTGGAAGATAGCTGTAGATAAATTCCAGTGCTTCAAATGGGTGAAA
GAAGCTATAATTTTATTAAAAAGGTGTCTTAGTTGATAATTTTATCATACATTTTTTCTCCAACTTGATAACT
TCAAGACTATGGGTAGGATTTGGATATAATGAGATTTTGAGCCATATAAGGTTAATGTTGTTTAGTAATTGTA
ATCTGGCAGGATATGTTTTCTTTGAACAGAGCTAAAACATGTCCCTAGATATGAATTTTAACAAGCTAAGTAT
AAACAGAACTAAGCTTGCAACTTTTCTATATTTCTATACTTCAGGATAAGCTTATAAACGCAGGTAATCCGTG
CAAGTGAACATATGTTTCATAAAAACAAATTATGCTGTCTTCATACTGATGTTGAAATAAGCAAGTCAAAGTT
CAATGGCAAAGAATTTGAGAATAGCTTAGGTTCTTGGCCCATGCACATTTTATGTTGTATATATTCTAACTAT
GACATGTTTGTACTGTTAGTTATTTGGTGCTCCACGGATTTATGAAAGAGATGCAAGGTCTTTTGGACTCATT
ACTGAAGACCCTTTCTTAAACTTTTCCACGGAAATTGACACCCAATGGTTTCGAGCAACTGATTTTACTCCAT
CATGTAGTATTGGACAATCTGCTGCTTTATGCTTGGAGATTCCCTACGGTCGCCAGCTCCCTAATTTTCATGA
TAAATTTGCTTACTTCAAAGAAATCAAGGGTAAATTTACATTGGTCAGTGGTTCTACTTATTCCTCCAATGTA
AACTTGGTACCTGTAGTTACACCTCCTCGAACCATCAACTTGCCATATACAATTTTGTTTAAGATAAATTTGT
TGGTACAACAAGGATGTCTTCCAGGCCCAGCTCTTGATATTAGTTTCTATCAGATGGTAGATTCTCAGATATA
CAATACTGCCGTCATAGATCATGCGTTAAAGAAACTTCTCCACTTGAAAGAGTGTTGCTATAACCCTTCAAAA
TGGTTAGATGAGGAATACAGAAAGTACTTCAAATTAAAGAATCCCCCCCAGCCACCTATTTTGACCTTGAATG
AAGGGTTAGTCTATGTACACAGGGTTCAAGTGACACCTTGTAAAGTTTACTTTTGTGGTCCAGAAGTTAACAT
TTCAAATCGTGTATTACGCCGGTATCCTGACTACATTGACAACTTTTTGCGTGTTTCATTTGTTGACGAGGAA
TTGGGTAAAATGTATTCAACTGAGTTGTCTCCACGTGCATCTTCTTCTTTGGAGGATGGAAAGACAAAAATTT
TTAAACGGATTCTTTCAGTTCTAAGAGATGGCATCACTATTGGTGATAAGAAGTTTGAGTTTCTAGCTTATTC
ATCTAGTCAATTACGGGAAAATGCTGCATGGATGTTTGCTCCAAAAAATGAACTTACTGCAGCTAAAATAAGG
CAATGGATGGGAGATTTTCATAATATACGAAATGTAGCCAAGTATGCTGCTAGACTAGGCCAATCCTTTGGTT
CATCAACAGAAACTTTAAGTGTCAGTAGACGTGAAGTTAAAGTTATTCCTGATATTGAAGTTGAATCAGGTAG
TGGTGTCAATTATGTCTTCTCTGATGGTATTGGGAAAATAGCAGCTAGTTTTGCTAGAAAAGTGGCTAAAAAA
TGTGGGATCAGGCATACACCATCTGCTTTTCAGATTCGTTATGCTGGTTTTAAAGGTGTTATTTCTGTTGATC
CTACCTCATCAGTAAAATTATCGCTAAGGAACAGCATGCTCAAGTATGAATCAACAGACACGAAGCTTGATGT
TTTATCATGGAGTAAATATCATCCTTGCTTTCTAAATCGTCAGTTGATTACTCTTTTGTCTACACTTGGAGTT
CAGGATCATGTTTTTGAGAGTAAACAACAGGAGTTGATTGATGAATTGGACACCATTTTAGTGATCCATTGA
AGGCTCAGCAGGCTCTTGAGCTAATGTCTCCAGGAGAGAATACCAAGATACTTAAGGAAATGATGTTGTGCGG
TTACAAACCTGATTCTGAACCTTTCTTAAGAATGATGTTGCACACATTCAGAGAATCAAAGTTGATGGAATTG
CGAATGAAGTCAAGGATCTTCATTCCAAATGGAAGAGCAATGATGGGATGTCTCGACGAAACAAGAAACTTGG
AATATGGGGAGGTATTTGTGCAGTGTTCTGCACATCAGCAGCTGCATGACGATCGCGTAATCTTTAAGAGAAT
AAAATCGAACCGGCATTTCATTGTAACTGGAACAGTTGTAGTGGCCAAAAACCCCTGCTTGCACCCAGGTGAT
GTGCGCGTTTTAACAGCCGTGGATGTACCATCACTGCATCACATGATAGATTGTGTGGTTTTCCACAAAAAG
GGTCAAGGTAAATGATCTATTTTAACATCAAAATTTACATGTCCAGTTCAAGTAAAATAAAATATATTTCTCC
TTTTCAGTCTTAGATATATGTTTATACTCGACTTAATGAATTCTTAACTGTGTGGCTAAGCATCTCTAATGTC
ATCATGTTTACTAGTAATTTTGCTTATCTTAGAAACTTCTTTTTTTTACTTGCCTTGAGGGGTGTCATAACT
CTAATTGATCTTACCTACCTTTATTCTCTATATTTCGTACTTTCTTCCTTCTCAAGTTGATAAAACCGTTTCT
CTTCATGCCTCTAGATAGCCAACACATCATCAGTGAACTAAAGTAAAACTATGTGTTGTTTTCTTCTCTGCCT
GCTGATTGTTTTGTCATAGCACTTGTCTTGTTTGATTCTTGCATGTTGATTGTTTCTGTCATAACACTTCTC
TTTCTATGTAAGACCTCATCCAAATGAATGCTCTGGAAGCGATCTAGATGGTGATATTTACTTCGTCTGTTGG
GACCCTGATTTGATTCCACCTCAACAAGTTGAACCAATGGATTATACCCTGTACCTAGCCAAGTACTAGATC
ATGATGTCACAATGGAGGTATGGTTTACAAGTGAACTTTGAACTGTTGTTATCATCAACAAGTATTTTAGAGG
AAAAAGGTTGTTCTATAGTGTAAATGTTGTAATGCAGGAGGTCCAGGAGTATTTTGCAAATTATATGGTCAAT
GACAGTTTAGGAATCATTGCCAATGCTCATACAGCTTTTGCAGATAAAGAGCCAAAGAAGCAATGAGCAATC
CTTGTATACAGCTCGCAAAACTATTCTCAATTGCAGTCGACTTTCCGAAAACTGGAGTCCCTGCTTTAATACC
TGCTAATCTAAGAGTAAAGAATATCCGGATTTCATGGATAAAGCCGACAAAGTGACATACGAGTCGGAGAAT
GTACTGGGGAAACTATTTAGAATGTTGGATAGCATTGGTCCAAACATTAAGAATATCAGGTCCTTCAACTATA
CGCCGGAGATGGCTCGGCAAGATTATGACCCTGACATGGAAGTTGAAGGTTTCGAGGAGTACCTCGACGATGC
AATATATCACAAGAACAACTATGACATGAGGGTTGGGAAATTTGATGCACTATCATAAGATCAAAACTGAGGCG
GAATTGATCAGTGGTGGTAGTTTGACGTCATCATTATCTTTCACCATGAAAAATGAAGCGGAATCGATTATCT
```

Fig. 1G

TGGCTGTGAAGTCGCTGCGAAAGGAGGCGAGGGGCTGGTTCAATGAGAAAGCAGACTTACATTATGGACATCA
TACTAATGTGTATGCAAGAGCTTCAGCATGGTATTTTGTTACATATCATCACACCTACTGGGGGTGGTCTGAT
GGCAGAAAGAATCATGGCCATTTTCTTAGCTTTCCATGGTGTGTTTATGATAAACTCATCCGTATCAAGCACC
GCAAAATTAATTGTAGAGCTCGCTATTGA

Fig. 2

Protein sequences SEQ ID Nos. 2 and 4

**SEQ ID No. 2 – *CsRDR1_II***
>Cucumis sativus_cs9930v2_emv_14138_protein sequence MGKTIQLFGFPSGVLQESVKTFVEGITGTGTIDAINTKRSKGGGRRVYAIIQFTDEEGAKSIISKATERLCYG
TSYLKAREMKHDILPDPLVFDYNFKALRLHLGCQISKESFSVLWTESNVSVDFGFELRKLYFFISYPRVDYML
VLRYENIWQVELHKPHGQSVDYLLIQLFGAPRIYERDARSFGLITEDPFLNFSTEIDTQWFRATDFTPSCSIG
QSAALCLEIPYGRQLPNFHDKFAYFKEIKGKFTLVSGSTYSSNVNLVPVVTPPRTINLPYTILFKINLLVQQG
CLPGPALDISFYQMVDSQIYNTAVIDHALKKLLHLKECCYNPSKWLDEEYRKYFKLKNPPQPPILTLNEGLVY
VHRVQVTPCKVYFCGPEVNISNRVLRRYPDYIDNFLRVSFVDEELGKMYSTELSPRASSSLEDGKTKIFKRIL
SVLRDGITIGDKKFEFLAYSSSQLRENAAWMFAPKNELTAAKIRQWMGDFHNIRNVAKYAARLGQSFGSSTET
LSVSRREVKVIPDIEVESGSGVNYVFSDGIGKIAASFARKVAKKCGIRHTPSAFQIRYAGFKGVISVDPTSSV
KLSLRNSMLKYESTDTKLDVLSWSKYHPCFLNRQLITLLSTLGVQDHVFESKQQELIDELDTIFSDPLKAQQA
LELMSPGENTKILKEMMLCGYKPDSEPFLRMMLHTFRESKLMELRMKSRIFIPNGRAMMGCLDETRNLEYGEV
FVQCSAHQQLHDDRVIFKRIKSNRHFIVTGTVVVAKNPCLHPGDVRVLTAVDVPSLHHMIDCVVFPQKGSRPH
PNECSGSDLDGDIYFVCWDPDLIPPQQVEPMDYTPVPSQVLDHDVTMEEVQEYFANYMVNDSLGIIANAHTAF
ADKEPKKAMSNPCIQLAKLFSIAVDFPKTGVPALIPANLRVKEYPDFMDKADKVTYESENVLGKLFRMLDSIG
PNIKNIRSFNYTPEMARQDYDPDMEVEGFEEYLDDAIYHKNNYDMRLGNLMHYHKIKTEAELISGGSLTSSLS
FTMKNEAESIILAVKSLRKEARGWFNEKADLHYGHHTNVYARASAWYFVTYHHTYWGWSDGRKNHGHFLSFPW
CVYDKLIRIKHRKINCRARY

**SEQ ID No. 4 – *CsRDR1_I***
>Cucumis sativus_cs9930v2_emv_14137_protein sequence MGKTIHISGFPSHVTADAVKNFLEGHTGPGTVYAIKVRPPKRGGGRLYAIVQFTSATQAELIISLANQRLWYG
SSYLKARATEVDIVPKPRTYMYTLEELLLCFGCQVSTEKFRVLWEGNVDLVTFGIGMRKMNFHLKYKSVEYRL
ELSYEIIWQIQLHCPRDQSMKYLLIQLSGAPRIYKKVAPNSGQIFDNPLLNFFKEASDDQWVRTTDFTSSCSI
GQSSSLCKLPNGRQLPPFKQNFAYYEEFEHEFRLIDEDANFSFCRDLAPIVDSRSHVLPYKILFKINALVQY
GCIPWPLLDASFYRLVERIITTRIEFVEHALEKLFHLKECNYDPSNFLTEQYRKYSRHPPNSPVISLDDGLVY
VRRVQITPCKVFFCGPEVNVSNRVLRHFSQYIDNFLRVSFVDEEWDKMRSTDLLPRMSSKSEDGKTDIYRRIL
SVLKNGIVIGDKTFQFLAFSSSQLRDNSLWMFASGPDIDAAYIRAWMGDFRHIKNPAKYAARLGQSFGSSTEA
LSVASNEREIIPDIEVQQGEIKYVFSDGIGKISSKFAKEVAAKCGFQAVPSAFQIRYGGYKGVVAVDPYSTIK
LSLRKSMCKFESDNTKLDVLGHSKYQPCFLNRQLITLMSTLGVRDEIFEKKQSEAVEQLDAILTDPLKAQEAL
ELMSPGENTNILKEMLKCGYQPDVEPYLSMMLQTFRASKLLELRTKSRIFIPNGRAMMGCLDETRTLEYGQVF
VQISSGRHRNLSESFAFNRIGREHHLVIEGNVTVAKNPCLHPGDVRVLKAVNIPGLYHMVDCVVFPQKGSRPH
PNECSGSDLDGDIYFVCWDTELIPSRQIPPMDYTPAPPNELDRDVTTEDIQEYFVNYMVNDSLGIIANAHTAF
ADKELFKARSSPCLELAKLFSVAVDFPKTGVPAIIPSHLYVKEFPDFMEKPDRPSYESNKVIGKLFRAVKDIA
PTLSHIRSFTRDVARRCYDCDMEVEGFEDYVEDAFYHKSNYDYKLGNLLDYYGIKSEAEVLSGSIMRMSKSFT
RRRDAEAINLAVRSLRKEARTWFNAREGADSNSDDLFAKASAWYYVTYHHSYWGCYNEGMKRDHYLSFPWCVY
DKLMQIKENNLRRRERAARLASFDRFGHVLNLGGS

COPY NUMBER VARIANT LEADING TO VIRUS RESISTANCE

RELATED APPLICATIONS AND INCORPORATION BY REFERENCE

This application is a continuation-in-part application of international patent application Serial No. PCT/EP2016/059297 filed Apr. 26, 2016, which published as PCT Publication No. WO 2017/054938 on Apr. 6, 2017, which claims benefit of NL patent application Serial No. 2015547 filed Oct. 2, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Mar. 9, 2018, is named 431040023543_SL.txt and is 47,699 bytes in size.

FIELD OF THE INVENTION

The present invention relates to a genetic determinant which leads to virus resistance in a plant. The invention further relates to a method for producing such a plant and a method for selecting such a plant. The invention also relates to a virus resistant plant or seed comprising the genetic determinant.

BACKGROUND OF THE INVENTION

Viruses constitute a major group of pathogens that infect plants, resulting in negative effects that influence aspects of crop cultivation such as plant growth, plant vigour, product quality, and yield potential. Like most eukaryotes, plants have established a general defense response against invading pathogens, such as viruses. Pathogenic viruses however are able to evade such defense response by using different suppressor mechanisms. By consequence, within the host plant species, specific defense responses have evolved to counteract the suppressor mechanism of the pathogenic viruses.

When a plant or crop is affected by disease, in many cases this will not just be by a single virus, but by a combination of two or more viruses or other pathogens, which only enlarges the problem. Many professionally cultivated crops have resistances against several pathogens by which they can be affected. One of the challenges of a breeding programme is to efficiently combine resistances that are most relevant to that specific crop, or that are for example relevant for a specific cultivation season or area of that crop.

In co-pending application PCT/EP2015/057409 a modified RDR1 gene is described which confers resistance to viruses, in particular against viruses of certain families and specifically against viruses of the Potyviridae, Bromoviridae and/or the Virgaviridae. The presence of this modified RDR1 gene in a *Cucumis sativus* plant results in resistance against Cucumber Vein Yellowing Virus (CVYV), and may contribute to resistance against other viruses, such as for instance Cucumber Green Mottle Mosaic Virus (CGMMV), Cucumber Mosaic Virus (CMV) and Zucchini Yellow Mosaic Virus (ZYMV).

Further research in *Cucumis sativus* that led to the invention showed however that resistance against CVYV and CGMMV were often present together, but that there were also recombinants that were either only resistant to CVYV or only resistant to CGMMV. Modification of the RDR1 gene alone was therefore not a guarantee to acquire resistance against both CVYV and CGMMV, and potentially other virus infections. Also, identification of the presence of the modified RDR1 gene was always predictive for resistance against CVYV, but was not always predictive for resistance against CGMMV. Something similar can be expected for some of the other viruses, and in some of the other crops in which the presence of the modified RDR1 gene contributes to virus resistance.

It was then established that in the genome of *Cucumis sativus* two closely linked RDR1 genes are located on chromosome 5. These two RDR1 genes are not exact copies, but are very similar, and are designated herein as CsRDR1_I or 14137, and CsRDR1_II or 14138. Furthermore, the two closely linked RDR1 genes are inversely oriented, more specifically meaning that they are linked to each other through their 3'-ends.

Citation or identification of any document in this application is not an admission that such document is available as prior art to the present invention.

SUMMARY OF THE INVENTION

It was surprisingly found that when this combination of two closely linked inversely oriented RDR1 genes was duplicated, resulting in two or more copies of the combination, and thus a total of four or more RDR1 genes, this duplication resulted in increased virus resistance in a plant. The presence of two or more copies of this combination is designated as a copy number variant, the presence of which copy number variant influences virus resistance.

The present invention thus provides a genetic determinant comprising at least two copies of a combination of two closely linked RDR1 genes, which two closely linked RDR1 genes are inversely oriented, and which genetic determinant leads to virus resistance when present in a plant.

The combination of two closely linked inversely oriented RDR1 genes is defined herein as 'the combination' or 'the RDR1 locus'. As used herein, 'closely linked' in relation to the two RDR1 genes that are present in the combination means that no recombination takes place between these two RDR1 genes. In one embodiment, the distance between the two RDR1 genes within the combination comprises not more than 3000 nucleotides. The nucleotides between the genes are not part of the sequences of said genes. No other genes are located between the two RDR1 genes that are present in the combination. The terms 'copy' and 'duplicate' represent the same and are used interchangeably herein. 'Duplication' and 'copied' as used herein comprise multiplication to two or more copies of the combination. Two or more copies are therefore different copy number variants of the combination of two RDR1 genes.

The genetic determinant of the invention can comprise two copies of the combination of two closely linked, inversely oriented, RDR1 genes. The genetic determinant can also comprise three copies of the combination, or four copies, or more than four copies. The presence of at least two copies of the combination leads to virus resistance in a plant. A plant may become resistant to a certain virus due to the presence of the genetic determinant of the invention, or the resistance of an already resistant plant may be increased. The level of resistance is as compared to an isogenic plant that has only a single version of the combination of two closely linked, inversely oriented, RDR1 genes. The presence of each additional copy of the combination in the genetic determinant may lead to an additional increase in the level of virus resistance. This means that for example a plant having four copies is more resistant than a plant having three copies, which in turn is more resistant than a plant having two copies.

The RDR1 locus that is duplicated in the genetic determinant of the invention optionally comprises one additional gene adjacent to one of the inversely oriented RDR1 genes, which additional gene is also duplicated as part of the combination to form a further version of the genetic determinant of the invention.

The two or more copies, or duplicates, of the combination of RDR1 genes in the genetic determinant of the invention can be present as tandem duplicates, meaning that the duplicates are located directly adjacent to each other on the chromosome. The duplicates are directly adjacent when no, or a maximum of 10, nucleotides are present in between the copies. Each duplicate optionally comprises one additional gene adjacent to one of the RDR1 genes. The duplicates can also be present as interspersed duplicates, which means that about one thousand, two thousand, or even six thousand nucleotides are present in between the duplicated copies. A larger chromosome segment can also be present between copies. Optionally, one of the duplicates can even be positioned on a different chromosome. The presence of multiple copies of the described combination as such within the genome of the plant is sufficient to form the genetic determinant of the invention.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The following detailed description, given by way of example, but not intended to limit the invention solely to the specific embodiments described, may best be understood in conjunction with the accompanying drawings.

FIGS. 1A-1G—Genomic sequences of SEQ ID No. 1, SEQ ID No. 3, and SEQ ID No. 5, including the coding sequence (CDS), which starts with the start codon ATG (bold in the sequence), and the sequence about 2 kb upstream of the start codon including the 5'-UTR and the promoter. Sequences are of *Cucumis sativus* CsRDR1_II, CS RDR1_I, and CsRDR1_II having an indel upstream of the start codon respectively.

FIG. 2—Protein sequences of SEQ ID No. 2 and SEQ ID No. 4, generated by the CDS's of CsRDR1_II and CsRDR1_I respectively, whereby CsRDR1_II with the indel, represented by SEQ ID No. 5, codes for the same protein as CsRDR1_II since the CDS is the same.

A: WGS read mapping of Geno3 to reference genome (pacbio);

B: WGS read mapping to BF11 reference (pacbio), CGMMV susceptible (S) and CVYV susceptible (S) lines;

C: WGS read mapping to BF11 reference (pacbio), CGMMV resistant (R) and CVYV susceptible (S) lines;

D: WGS read mapping to BF11 reference (pacbio), CGMMV resistant (R) and CVYV resistant (R) lines.

Figure 3A:
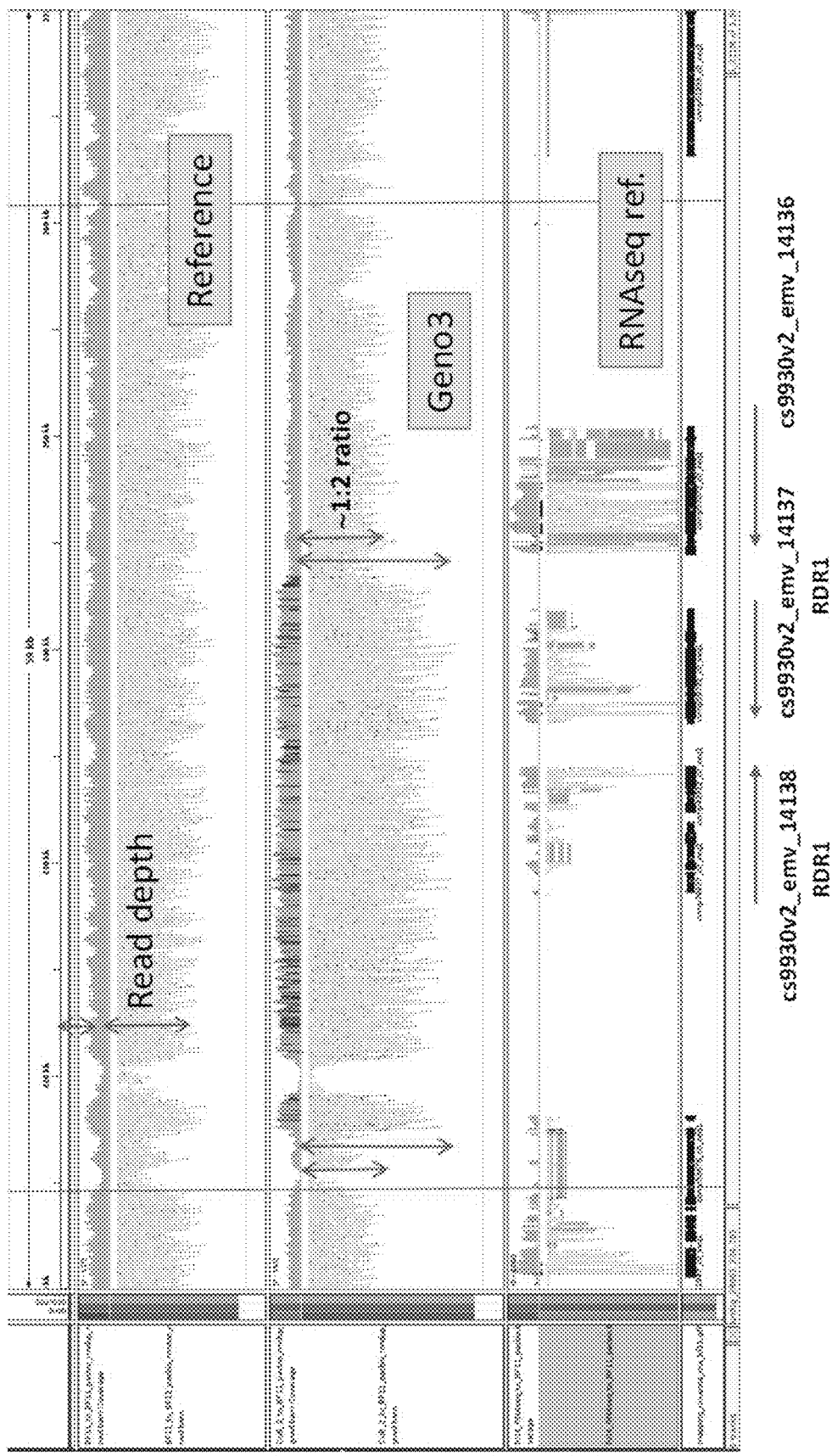
FIGS. 3A-3D—Read depth analysis of sequencing data from various lines that were susceptible to both CVYV and CGMMV, were resistant to CGMMV and susceptible to CVYV, or were resistant to both viruses.
Figure 3B:
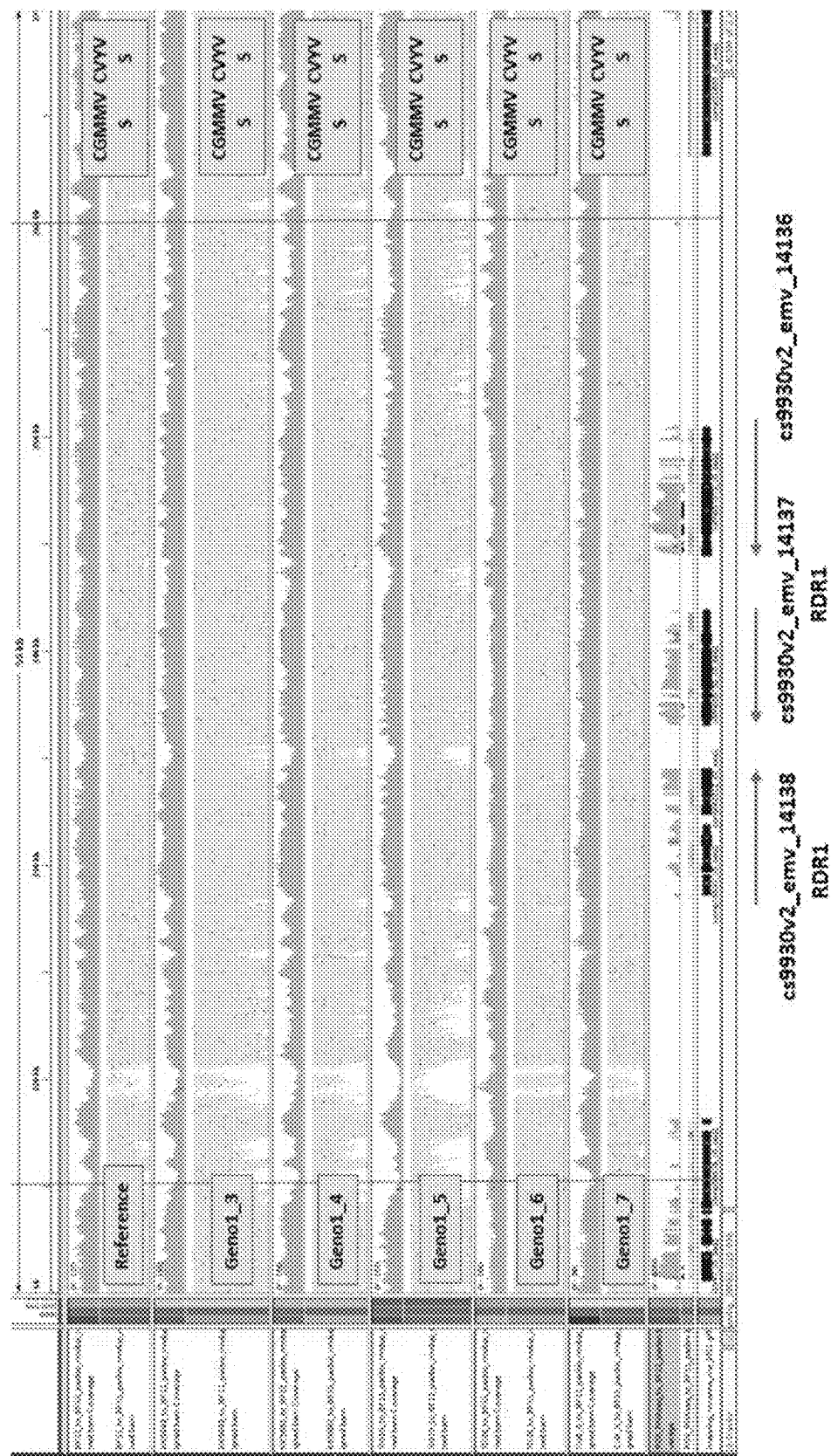
Figure 3C:
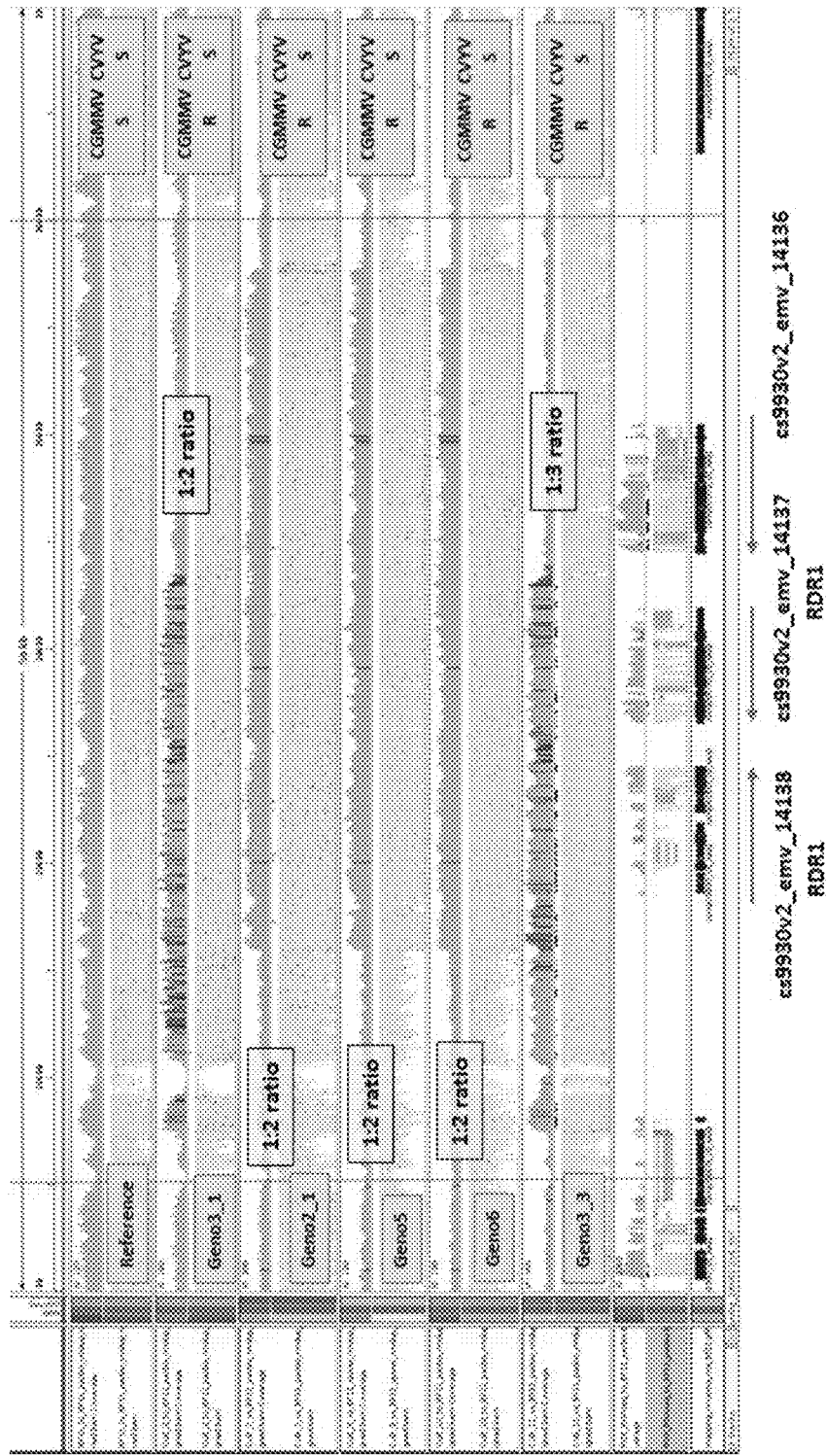
Figure 3D:
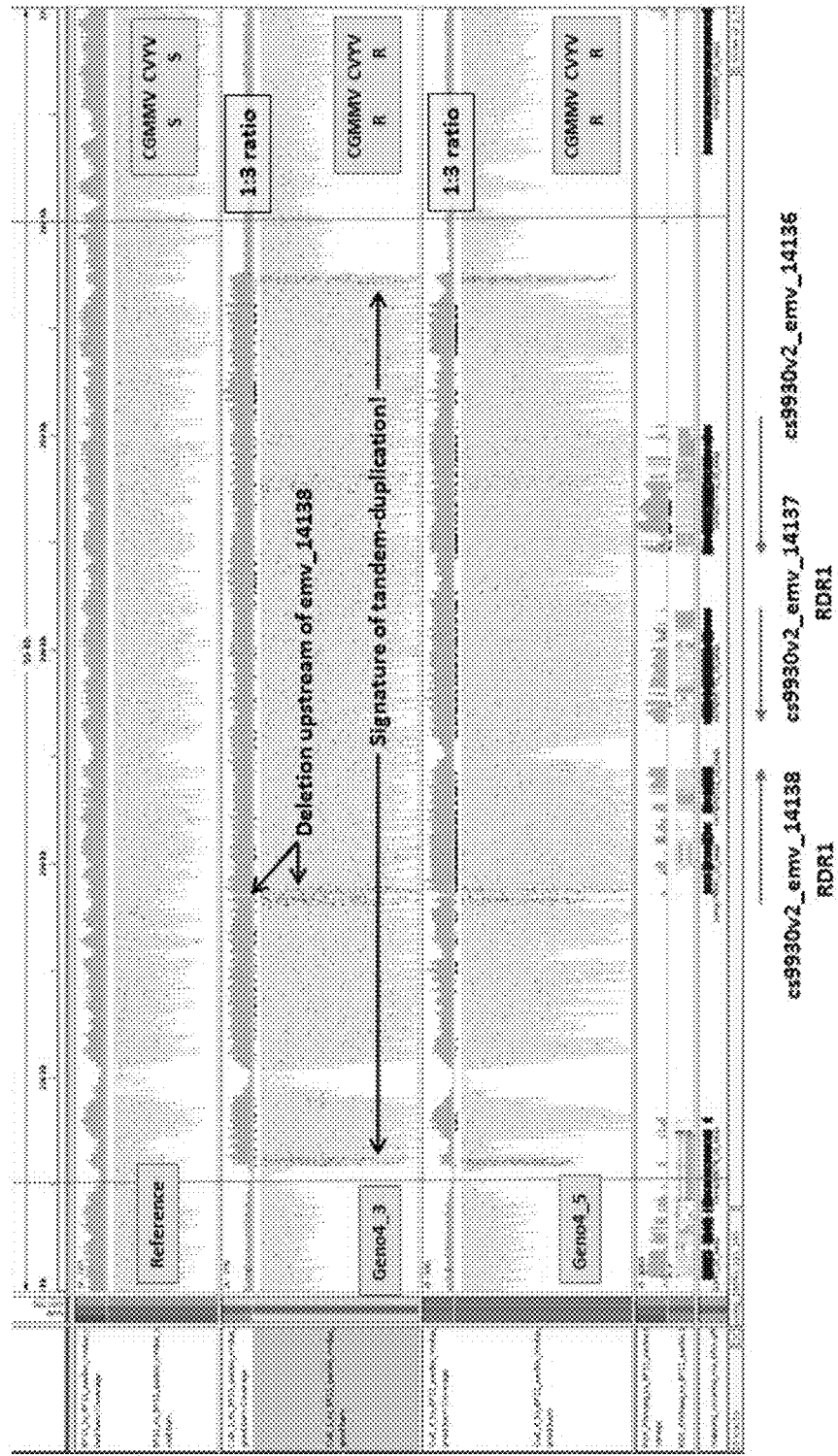
Figure 4:
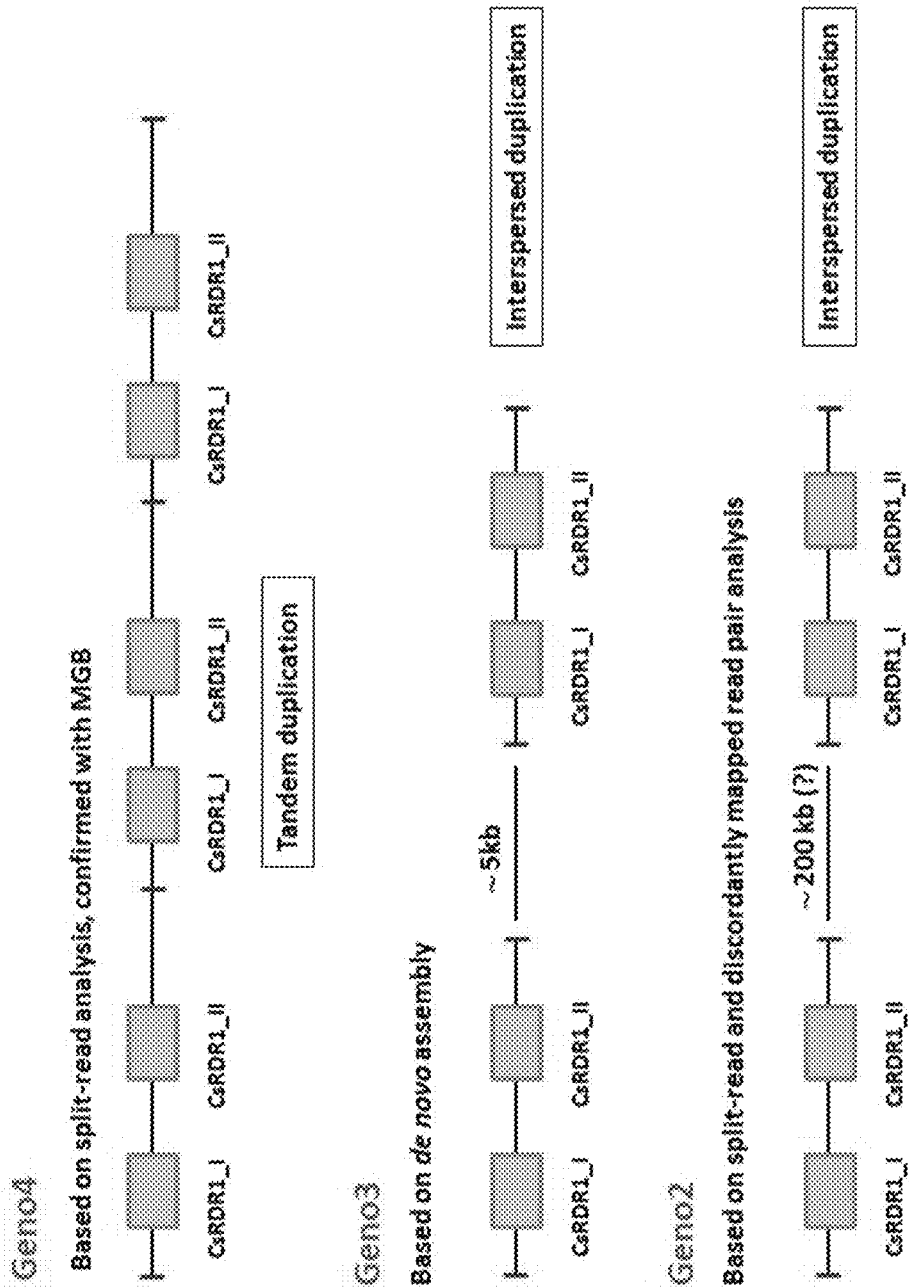

FIG. 4—Possible locations of copies of the combination of RDR1 genes within the genome, in relation to each other. For 'Geno4' a genetic determinant with 3 copies is depicted, and for 'Geno2' and 'Geno3' genetic determinants having 2 copies are depicted.

DETAILED DESCRIPTION OF THE INVENTION

Copy number variants (CNVs) are relatively recently identified as one of the major potential sources of genetic variation. The approach for determining the presence of CNVs in a genome to be able to identify their effect is however very different from identification of other variations within genes, such as modifications that are present within genes. As for the latter, usually analysis of sequences leads to the identification of differences between the sequences in the comparison. These differences are subsequently used for the development of markers that are linked to a genomic region that comprises a modification, or markers that comprise the mutation itself. This is however not feasible for establishing the presence of CNVs, since these are not based on differences in the nucleotide sequence of a gene. A copy number variant has to be identified by determining the repetition of specific sequences within a genome, and especially sequences that form genes or parts of genes. These variations in copy number can be present close to each other, for example on the same chromosome, but they can also be positioned on different locations in the genome. The majority of genetic variation that is caused by CNVs, and especially their impact on and relation to specific phenotypic traits, is not yet revealed.

In a preferred embodiment the genetic determinant of the invention comprises at least three copies of the combination of two closely linked, inversely oriented, RDR1 genes.

In one embodiment the sequence of at least one of the RDR1 genes of the combination is represented by SEQ ID No. 1, which is the sequence of CsRDR1_II, or has a sequence with a sequence identity of, in order of increased preference, at least 70%, 75%, 80%, 85%, 90%, 95%, 98%, or 99% to SEQ ID No. 1. Said similar sequence should underlie a functionally homologous gene of the CsRDR1_II gene. Alternatively, at least one of the RDR1 genes of the combination has a sequence that encodes a protein that is represented by SEQ ID No. 2, or encodes a protein that has a sequence identity of, in order of increased preference, at least 70%, 75%, 80%, 85%, 90%, 95%, 98%, or 99% to SEQ ID No. 2.

In one embodiment, the sequence of at least one of the RDR1 genes of the combination is represented by SEQ ID No. 3, which is the sequence of CsRDR1_I, or has a sequence with a sequence identity of, in order of increased preference, at least 70%, 75%, 80%, 85%, 90%, 95%, 98%, or 99% to SEQ ID No. 3. Said similar sequence should underlie a functionally homologous gene of the CsRDR1_I gene. Alternatively, at least one of the RDR1 genes of the combination has a sequence that encodes a protein that is represented by SEQ ID No. 4, or encodes a protein that has a sequence identity of, in order of increased preference, at least 70%, 75%, 80%, 85%, 90%, 95%, 98%, or 99% to SEQ ID No. 4.

In a particular embodiment the combination comprises one RDR1 gene represented by SEQ ID No. 1 or by a sequence having, in order of increased preference, at least 70%, 75%, 80%, 85%, 90%, 95%, 98%, or 99% sequence identity thereto, and one RDR1 gene represented by SEQ ID No. 3 or by a sequence having, in order of increased preference, at least 70%, 75%, 80%, 85%, 90%, 95%, 98%, or 99% sequence identity thereto.

In an alternative embodiment the combination comprises one RDR1 gene that encodes a protein as represented by SEQ ID No. 2 or encodes a protein having, in order of increased preference, at least 70%, 75%, 80%, 85%, 90%, 95%, 98%, or 99% sequence identity thereto, and one RDR1 gene that encodes a protein as represented by SEQ ID No. 4 or encodes a protein having, in order of increased preference, at least 70%, 75%, 80%, 85%, 90%, 95%, 98%, or 99% sequence identity thereto.

A genetic determinant comprising the particular combination of SEQ ID No. 1 and SEQ ID No. 3 leads to resistance to Cucumber Green Mottle Mosaic Virus when present in a Cucumis sativus plant. In a preferred embodiment said genetic determinant comprises at least three copies of the particular combination of SEQ ID No. 1 and SEQ ID No. 3.

In one embodiment the combination comprises one RDR1 gene represented by SEQ ID No. 1 or by a sequence having, in order of increased preference, at least 70%, 75%, 80%, 85%, 90%, 95%, 98%, or 99% sequence identity thereto, and one RDR1 gene that encodes a protein as represented by SEQ ID No. 4 or encodes a protein having, in order of increased preference, at least 70%, 75%, 80%, 85%, 90%, 95%, 98%, or 99% sequence identity thereto.

In one embodiment the combination comprises one RDR1 gene that encodes a protein as represented by SEQ ID No. 2 or encodes a protein having, in order of increased preference, at least 70%, 75%, 80%, 85%, 90%, 95%, 98%, or 99% sequence identity thereto, and one RDR1 gene represented by SEQ ID No. 3 or by a sequence having, in order of increased preference, at least 70%, 75%, 80%, 85%, 90%, 95%, 98%, or 99% sequence identity thereto.

SEQ ID Nos. 1 and 3 represent the wild-types of the CsRDR1_II and CsRDR1_I genes of *Cucumis sativus*, and the corresponding proteins represent the wild-type proteins. Genes that are the functional homologue of CsRDR1_I or CsRDR1_II in other crops have at least 70% up to 99% sequence identity with one of these RDR1 genes of *Cucumis sativus*.

In certain instances the expression of at least one of the RDR1 genes of the combination in the genetic determinant can be increased as compared to the expression when only a single version of the wild-type is present. The expression of one or both of the RDR1 genes of the combination can for example be increased due to the presence of at least two copies, optionally three, four, or more copies of the combination in the genetic determinant.

The expression of at least one of the RDR1 genes can alternatively be increased due to a modification in the wild-type nucleotide sequence of said gene. Such a modification comprises for example a modification upstream of the start codon of the gene, in particular a modification in the promoter or the 5'-UTR.

The increased expression can be an increase of the mRNA level of the RDR1 gene, or an increase of the level of the RDR1 protein, or an increase of the activity of the RDR1 protein.

Increased expression of a gene that is present in a plant can be measured in steady state situation, which in relation to the function of this gene means a situation wherein no virus infection is present in the plant. Alternatively increased expression of a gene that is incorporated in a plant can be measured in an infected state situation, whereby a virus infection is present in the plant.

In a specific embodiment the modification upstream of the start codon of one of the RDR1 genes in the combination resulting in increased expression and virus resistance is an indel. The indel that leads to increased expression is suitably an indel resulting in a modified gene sequence represented by SEQ ID No. 5. Downstream from the start codon ATG, SEQ ID No. 5 has the same sequence as SEQ ID No. 1. The invention also relates to a genetic determinant whereby the sequence upstream of the start codon of one of the CsRDR1 genes in the combination has, in order of increased preference, at least 70%, 75%, 80%, 85%, 90%, 95%, 98%, or 99% sequence identity to the sequence upstream of the start codon of SEQ ID No. 5.

In a particular embodiment the genetic determinant comprises one CsRDR1 gene represented by SEQ ID No. 3 or having, in order of increased preference, at least 90%, 95%, 98%, 99% sequence identity thereto, and one CsRDR1 gene represented by SEQ ID No. 5 or having, in order of increased preference, at least 90%, 95%, 98%, 99% sequence identity thereto.

A genetic determinant comprising the particular combination of SEQ ID No. 3 and SEQ ID No. 5 leads to resistance to Cucumber Green Mottle Mosaic Virus and to Cucumber Vein Yellowing Virus when present in a *Cucumis sativus* plant. In a preferred embodiment said genetic determinant comprises at least three copies of the particular combination of SEQ ID No. 3 and SEQ ID No. 5. The CsRDR1 genes represented by SEQ ID No. 3 and SEQ ID No. 5 need not necessarily have the exact sequence of these SEQ ID's in said resistant *Cucumis sativus* plant, but can also show at least 90%, 95%, 98%, 99% sequence identity thereto.

As used herein, the percentage 'sequence identity' is the percentage of nucleotides or amino acids that is identical between two sequences after proper alignment of those sequences. The person skilled in the art is aware of how to align sequences. To obtain the most significant result, the best possible alignment that gives the highest sequence identity score should be obtained. The sequences are compared over the length of the shortest sequence in the assessment.

A high percentage of sequence identity is commonly assumed to point to a homologous sequence. A genetic determinant comprising RDR1 genes having a sequence identity percentage as claimed is part of the invention if said similar sequence is functionally homologous. Functionally homologous means that it is a gene sequence that leads to a protein that has a similar function as the RDR1 genes that were identified in *Cucumis sativus*. A similar sequence is a sequence has at least 70%, up to 99%, sequence identity to SEQ ID No. 1 and/or SEQ ID No. 3 and/or SEQ ID No. 5. For this invention 'functionally homologous' means that the gene or protein is involved in virus resistance.

An 'indel' as used herein can represent an insertion, a deletion, or a combination of both. Preferably, the indel in one of the RDR1 genes in the combination, resulting in increased expression, comprises at least a deletion.

The presence of the genetic determinant of the invention in a plant suitably leads to resistance to a virus of the family Potyviridae, Bromoviridae, and/or Virgaviridae. Virus species belonging to these families that cause major problems by infecting a large number of cultivated crops are for example, but not limited to, Cucumber Vein Yellowing Virus (CVYV), Cucumber Mosaic Virus (CMV), Zucchini Yellow Mosaic Virus (ZYMV), *Papaya* Ringspot Virus (PRSV), Watermelon Mosaic Virus (WMV), Cucumber Green Mottle Mosaic Virus (CGMMV), Tobacco Mosaic Virus (TMV), Tomato Mosaic Virus (ToMV), Pepper Mild Mottle Virus (PMMoV), Pepper Mottle Virus (PepMoV), Potato Virus Y (PVY), Soybean Mosaic Virus (SMV), and Maize Dwarf Mosaic Virus (MDMV).

Plant species that have in their genome RDR1 genes that are homologous to SEQ ID No. 1 and/or SEQ ID No. 3, and are therefore particularly suitable for acquiring a genetic determinant of the invention, belong to various plant families such as Cucurbitaceae, Solanaceae, Brassicaceae, Apiaceae, Fabaceae, Amaranthaceae, and Asteraceae. Crop species suitable for acquiring a genetic determinant of the invention can specifically be selected from any of the following: *Phaseolus vulgaris, Beta vulgaris, Brassica oleracea, Daucus carota, Lactuca sativa, Cucumis melo, Cucumis sativus, Cucumis pepo, Spinacia oleracea, Solanum lycopersicum, Capsicum annuum*, and *Citrullus lanatus*.

The present invention relates to a method for producing a virus resistant plant comprising introducing a genetic determinant that has at least two copies of a combination of two closely linked RDR1 genes, which two closely linked RDR1 genes are inversely oriented, in a plant. The genetic determinant can be introduced from another plant which comprises the genetic determinant through commonly used breeding techniques such as crossing and selection when the plants are sexually compatible. Such introduction can be from a plant of the same species, that usually can be crossed easily, or from a plant of a related species. Difficulties in crossing can be overcome through techniques known in the art such as embryo rescue, or cis-genesis can be applied. Suitably markers can be developed for the genetic determinant to follow the incorporation of that genetic determinant into another plant.

The above method can in particular be used to introduce the genetic determinant of the invention into a plant species that is suitable for incorporation of such genetic determinant. In a particular embodiment the genetic determinant of the invention can be introduced from a *Cucumis sativus* plant comprising the genetic determinant into a *Cucumis sativus* plant lacking the genetic determinant using standard breeding methods. In *Cucumis sativus* the genetic determinant can comprise two, three, four or more copies of the combination of two inversely oriented RDR1 genes. Introduction of the genetic determinant in *Cucumis sativus* leads to resistance to Cucumber Green Mottle Mosaic Virus. When one of the RDR1 genes in the combination is represented by SEQ ID No. 5, the presence of the genetic determinant in *Cucumis sativus* leads to resistance to Cucumber Green Mottle Mosaic Virus and to resistance to Cucumber Vein Yellowing Virus.

Alternatively the genetic determinant of the invention can be introduced by increasing the copy number of closely linked inversely oriented RDR1 genes that are already present in the genome of a plant, or they can be transferred from another, sexually incompatible, plant, for example by using transgenic modification. Techniques that can suitably be used for modification of the copy number of a gene or a combination of genes, or for the transfer of multiple copies of RDR1 genes from other plants, comprise general plant transformation techniques known to the skilled person, such as the use of an *Agrobacterium*-mediated transformation method. Other genome editing methods such as the use of a CRISPR/Cas system might also be employed.

The invention further provides a plant comprising the genetic determinant of the invention, which plant is resistant to one or more viruses due to the presence of the genetic determinant. A plant of the invention is preferably resistant to one or more viruses of the family Potyviridae, Bromoviridae, and/or of the family Virgaviridae.

The invention also relates to a seed comprising the genetic determinant of the invention, wherein the plant grown from the seed is resistant to one or more viruses, in particular to one or more viruses of the family Potyviridae, Bromoviridae, and/or the family Virgaviridae.

A plant or a seed of the invention is a plant or a seed in which two or more copies of a combination of two inversely oriented RDR1 genes are present, which presence results in virus resistance, for example a plant or a seed of a species selected from the group consisting of *Phaseolus vulgaris, Beta vulgaris, Brassica oleracea, Daucus carota, Lactuca sativa, Cucumis melo, Cucumis sativus, Spinacia oleracea, Solanum lycopersicum*, and *Citrullus lanatus*.

A *Cucumis sativus* plant comprising the genetic determinant of the invention preferably is resistant against Cucumber Green Mottle Mosaic Virus, optionally in combination with resistance to Cucumber Vein Yellowing Virus.

The present invention also relates to a method for selecting a virus resistant plant, comprising determining the copy number of a combination of two RDR1 genes that are inversely present, and selecting a plant that comprises at least two copies of said combination as a virus resistant plant. A plant comprising at least two copies of said combination comprises the genetic determinant of the invention. In a preferred embodiment a plant comprising at least three copies of the combination is selected as a virus resistant plant.

Various methods based on sequencing of the genome have been developed to identify copy number variants (CNVs), and it is known to the person skilled in the art how to establish the presence of copy number variants within a genome of a plant. Straightforward strategies for CNV detection based on next generation sequencing data are for example (1) read depth analysis, (2) split-read analysis, (3) discordantly mapped read pair analysis, and (4) de novo genome assembly.

In the present research a tool was used to detect local copy number variation of the combination of the two RDR1 genes that were identified in the region of relevance in *Cucumis sativus*. Subsequently qPCR was used to also determine the expression level of the genes in the combination. Results of both the variation in copy number that was identified, and of the expression analysis, were linked to virus resistance of the plants (Example 1). In this ways the relation between genotype and phenotype was established.

In one embodiment the invention relates to a method for selecting a virus resistant plant, comprising determining the copy number of a combination of two RDR1 genes that are inversely present, and selecting a plant that comprises at least two copies of said combination as a virus resistant plant, wherein the combination of two closely linked RDR1 genes comprises at least one RDR1 gene that is represented by SEQ ID No. 1 or has a sequence identity of at least 70% thereto, and/or at least one RDR1 gene that is represented by SEQ ID No. 3 or has a sequence identity of at least 70% thereto.

In one embodiment the invention relates to a method for selecting a virus resistant plant, comprising determining the copy number of a combination of two RDR1 genes that are inversely present, and selecting a plant that comprises at least two copies of said combination as a virus resistant plant, wherein the combination of two closely linked RDR1 genes comprises at least one RDR1 gene that is represented by SEQ ID No. 3 or has a sequence identity of at least 70% thereto, and/or at least one RDR1 gene that is represented by SEQ ID No. 5 or has a sequence identity of at least 70% thereto.

In one embodiment the invention relates to a method for selecting a *Cucumis sativus* plant that is resistant to Cucumber Green Mottle Mosaic Virus, comprising determining the copy number of a combination of two RDR1 genes that are inversely present, and selecting a plant that comprises at least two copies, preferably at least three copies, of said combination as a CGMMV resistant plant, wherein the combination of two closely linked RDR1 genes comprises CsRDR1_II represented by SEQ ID No. 1, or a gene that has at least 90% sequence identity thereto, and CsRDR1_I, represented by SEQ ID No. 3, or a gene that has at least 90% sequence identity thereto.

In one embodiment the invention relates to a method for selecting a *Cucumis sativus* plant that is resistant to Cucumber Green Mottle Mosaic Virus and to Cucumber Vein Yellowing Virus, comprising determining the copy number of a combination of two RDR1 genes that are inversely present, and selecting a plant that comprises at least two copies, preferably at least three copies, of said combination as a CGMMV and CVYV resistant plant, wherein the combination of two closely linked RDR1 genes comprises a modified CsRDR1_II, represented by SEQ ID No. 5, or a gene that has at least 90% sequence identity thereto, and CsRDR1 represented by SEQ ID No. 3, or a gene that has at least 90% sequence identity thereto.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Identification of Copy Number Variants for RDR1 Genes in *Cucumis sativus* Related to Virus Resistance In previous research two closely linked, inversely oriented, RDR1 genes were identified on chromosome 5 of the *Cucumis sativus* genome. At least one of these RDR1 genes was, when modified, determined to be involved in conferring resistance to CVYV. Although there appeared to be a linkage with resistance to CGMMV, recombinants having only CGMMV or only CVYV resistance could be observed. Markers that were developed for the modified RDR1 gene were predictive for the CVYV resistance, but not always for the CGMMV resistance.

Whole genome sequencing (WGS) was subsequently done on a number of lines that were susceptible, or had one or both resistances. More than 250 additional markers were developed based on sequence differences in the region of interest. Again, also the analysis of these data and the application of the new markers did not result in better markers for the CGMMV resistance. This led to the assumption that something different than a modification in or around the gene on the chromosome 5 region might be leading to the CGMMV resistance, and it was decided to take a different approach.

The WGS data of the various lines were then mapped and subsequently analyzed using WGS read alignment visualization tools, and compared against an internally generated reference genome sequence of *Cucumis sativus*. Using this, the read depth of the sequence with the two RDR1 genes was observed. It was highly interestingly found that the read-depth of the specific sequence that has the two RDR1 genes was around two times or even three times higher for certain material when compared to the reference genome (FIGS. 3A-D).

To confirm this information a large number of 61 lines having CGMMV and CVYV resistance in various combinations, or being susceptible to both, were resequenced and a qPCR was performed using the available data. The qPCR data were analyzed using the 'delta delta Cq' method (ddCq), with efficiency correction. The threshold was calculated using suitable software, which is commonly known, for both target genes CsRDR1_I and CsRDR1_II, as well as for the reference gene. The following formula was used to calculate the eventual fold changes, which also indicates copy number variation:

$$\frac{\text{Sample } A}{\text{Sample } B} = \frac{(1 + E_{ref})^{CqA_{ref} - CqB_{ref}}}{(1 + E_{tar})^{CqA_{tar} - CqB_{tar}}}.$$

The different methods eventually led to the same result, and confirmed the presence of copy number variants for the combination of the two closely linked, inversely oriented, RDR1 genes in the genome of *Cucumis sativus*.

Example 2: Determination of the Location of the Different Copies

The location within the *Cucumis sativus* genome of the different copies was determined by a combined strategy, which includes split-read analysis, discordantly mapped read pair analysis, and de novo genome assembly. Based on this analysis, it was determined that the multiple copies of the RDR1 combination in the *Cucumis sativus* genome in some backgrounds are present as tandem repeats. This was determined by split-read analysis, but also verified with the use of an MGB assay that confirmed the presence of overlapping sequences. Other backgrounds showed that the copies were present on the same chromosome, but with around 1000 up to 6000 bp in between. This was done through de novo genome assembly. A third result showed that the copies can be even further away, possibly with around 200 kb in between, but a location on a different chromosome is also still feasible. To obtain this result, split-read analysis was combined with discordantly mapped read pair analysis. The combined results are visualized in FIG. 4.

Example 3: Linking Resistance to the Presence of Copy Number Variation

The lines that were analyzed in Examples 1 and 2 were also phenotyped for resistance to CVYV and to CGMMV. A bio-assay was performed using commonly known inoculation and observation methods for evaluating the resistance. For CGMMV two repetitions were carried out. CVYV resistance score was based on several bio-assays in different years.

Subsequently for each line the genotypic data indicating the copy number and the presence or absence of an indel, and the phenotypes indicating virus resistance were compared with each other to be able to draw conclusions. Results of certain representative lines are presented in Table 1.

'Geno1' refers to plants in which only one version of the combination of two closely linked inversely oriented RDR1 genes is present, so there are no multiple copies. 'Geno2' is a genetic background in which 2 copies are present, but they are located far from each other in the genome, probably around 200 kb or even more in between. Geno3' is a genetic background that does not have the indel in CsRDR1_II that is known to lead to CVYV. The copies in this background are located at a distance of between 1000 and 6000 bp from each other. 'Geno4' is a genetic background in which the copies of the combination of RDR1 genes are tandem duplications. Also, CsRDR1_II in this background has the indel that leads to CVYV resistance.

'R' means that in that test all plants were resistant. A score of 8/2/0 means that 8 plants are resistant, i.e. without symptoms, 2 plants show light symptoms, and 0 plants are susceptible.

TABLE 1

Copy number in relation to CVYV and CGMMV resistance, and gene expression

| | COPY NUMBER | | | EXPRESSION | | RESISTANCE | | |
|---|---|---|---|---|---|---|---|---|
| | Calculated CNV | | | | | | | |
| Reference | calculated cnv WGS | qPCR | copy number | 14138 | 14137 | CVYV | CGMMV-t1 | CGMMV-t2 |
| Geno1_1 | 1.1 | 0.87 | | −1.31 | −0.81 | S | S | S |
| Geno1_2 | 1.11 | 0.93 | | −0.64 | −0.55 | S | S | S |
| Geno2_1 | 2.19 | 1.92 | 2x | 0.9 | −1.32 | S | 8/2/0 | 8/2/0 |
| Geno3_1 | 2.02 | 1.86 | 2x | 1.05 | −0.33 | S | R | R |
| Geno4_1 | 1.08 | 1.02 | | 2.29 | −0.68 | R | S | S |
| Geno4_2 | 2.13 | 1.99 | 2x | 3.73 | −1.14 | R | R | R |
| Geno4_3 | 3.21 | 3.13 | 3x | 3.56 | −0.47 | R | R | R |
| Geno4_4 | 3.03 | 3.2 | 3x | 4.54 | −0.22 | R | R | 3/7/0 |

Based on these results it was concluded that the presence of multiple copies of the combination of RDR1 genes leads to resistance to CGMMV. When the indel in one of the two RDR1 genes is present (Geno4) it gives only CVYV resistance when just 1 version is present (Geno4_1). Only when two or more copies are present there is resistance to both CVYV and CGMMV. No copies and no indel gives susceptibility to both viruses (Geno1). Geno2_1 and Geno3_1 show that CGMMV resistance can be present independent of CVYV resistance.

The invention is further described by the following numbered paragraphs:

1. Genetic determinant comprising at least two copies of a combination of two closely linked RDR1 genes, which two closely linked RDR1 genes are inversely oriented, and which genetic determinant leads to virus resistance when present in a plant.

2. Genetic determinant of paragraph 1, comprising three, four, or more copies of the combination of two closely linked inversely oriented RDR1 genes.

3. Genetic determinant of paragraph 1 or 2, wherein
   a) at least one of the RDR1 genes in the combination is represented by SEQ ID No. 1 or has a sequence identity of at least 70% thereto; or
   b) at least one of the RDR1 genes in the combination encodes a protein represented by SEQ ID No. 2 or encodes a protein that has a sequence identity of at least 70% to SEQ ID No. 2.

4. Genetic determinant of paragraph 1 or 2, wherein
   a) at least one of the RDR1 genes in the combination is represented by SEQ ID No. 3 or has a sequence identity of at least 70% thereto; or
   b) at least one of the RDR1 genes in the combination encodes a protein represented by SEQ ID No. 4 or encodes a protein that has a sequence identity of at least 70% to SEQ ID No. 4.

5. Genetic determinant as paragraphed paragraph 3 or 4, wherein
   a) one of the RDR1 genes in the combination is represented by SEQ ID No. 1 or has a sequence identity of at least 70% thereto, and one of the RDR1 genes in the combination is represented by SEQ ID No. 3 or has a sequence identity of at least 70% thereto; or b) one of the RDR1 genes in the combination encodes a protein represented by SEQ ID No. 2 or a protein that has a sequence identity of at least 70% thereto, and one of the RDR1 genes encodes a protein represented by SEQ ID No. 4 or a protein that has a sequence identity of at least 70% thereto.

6. Genetic determinant of any of the paragraphs 1-5, wherein at least one of the RDR1 genes in the combination has an indel upstream of the start codon.

7. Genetic determinant of any of the paragraphs 1-6, wherein the distance between the two RDR1 genes that are inversely present is not more than 3000 bp.

8. Genetic determinant of any of the paragraphs 1-7, wherein the distance between copies of combinations of two RDR1 genes is not more than 6000 bp, preferably not more than 1000 bp, most preferably 0 bp.

9. Genetic determinant of any of the paragraphs 1-8, wherein one of the RDR1 genes is CsRDR1_II, represented by SEQ ID No. 1, or has at least 90% sequence identity thereto, and one of the RDR1 genes is CsRDR1_I, represented by SEQ ID No. 3, or has at least 90% sequence identity thereto, the presence of which genetic determinant in a *Cucumis sativus* plant leads to resistance to Cucumber Green Mottle Mosaic Virus.

10. Genetic determinant of any of the paragraphs 6-8, wherein one of the RDR1 genes is CsRDR1_I, represented by SEQ ID No. 3, or has at least 90% sequence identity thereto, and one of the RDR1 genes is a modified CsRDR1_II, represented by SEQ ID No. 5, or has at least 90% sequence identity thereto, the presence of which genetic determinant in a *Cucumis sativus* plant leads to resistance to Cucumber Green Mottle Mosaic Virus and Cucumber Vein Yellowing Virus.

11. Method for producing a virus resistant plant comprising introducing the genetic determinant of any of the paragraphs 1-10 into a plant.

12. Method for selecting a virus resistant plant, comprising determining the copy number of a combination of two closely linked RDR1 genes that are inversely present, and selecting a plant that comprises at least two copies, preferably at least three copies of said combination as a virus resistant plant comprising the genetic determinant of any of the paragraphs 1-10.

13. Method of paragraph 11 or 12 wherein the plant belongs to a species selected from the group consisting of *Phaseolus vulgaris, Beta vulgaris, Brassica oleracea, Daucus carota, Lactuca sativa, Cucumis melo, Cucumis sativus, Cucumis pepo, Spinacia oleracea, Solanum lycopersicum, Capsicum annuum*, and *Citrullus lanatus*.

14. Method of paragraph 11, 12, or 13 wherein the virus is of the family Potyviridae, Bromoviridae, and/or of the family Virgaviridae.

15. Method of any of the paragraphs 11-14, wherein the combination of two closely linked RDR1 genes comprises at least one RDR1 gene that is represented by SEQ ID No. 1 or has a sequence identity of at least 70% thereto, and/or at least one RDR1 gene that is represented by SEQ ID No. 3 or has a sequence identity of at least 70% thereto.

16. Method of any of the paragraphs 11-14, wherein the combination of two closely linked RDR1 genes comprises at least one RDR1 gene that is represented by SEQ ID No. 3 or has a sequence identity of at least 70% thereto, and/or at least one RDR1 gene that is represented by SEQ ID No. 5 or has a sequence identity of at least 70% thereto.

17. Method of any of the paragraphs 11-16, wherein the virus resistant plant is a *Cucumis sativus* plant which is resistant to Cucumber Green Mottle Mosaic Virus, and optionally resistant to Cucumber Vein Yellowing Virus.

18. Method of paragraph 15 or 17, wherein the combination of two closely linked RDR1 genes comprises CsRDR1_II, represented by SEQ ID No. 1, or a gene that has at least 90% sequence identity thereto, and CsRDR1_I, represented by SEQ ID No. 3, or a gene that has at least 90% sequence identity thereto, and wherein the selected virus resistant plant is a *Cucumis sativus* plant comprising two copies, preferably three or more copies, of said combination, the presence of which leads to resistance to Cucumber Green Mottle Mosaic Virus.

19. Method of paragraph 16 or 17, wherein the combination of two closely linked RDR1 genes comprises a modified CsRDR1_II, represented by SEQ ID No. 5, or a gene that has at least 90% sequence identity thereto, and CsRDR1_I, represented by SEQ ID No. 3, or a gene that has at least 90% sequence identity thereto, and wherein the selected virus resistant plant is a *Cucumis sativus* plant comprising at least two copies, preferably at least three copies, of said combination, the presence of which leads to resistance to Cucumber Green Mottle Mosaic Virus resistance and to Cucumber Vein Yellowing Virus.

16. Plant, which is resistant to one or more viruses due to the presence in its genome of the genetic determinant of any of the paragraphs 1-10.

17. Seed, wherein a plant grown from the seed is resistant to one or more viruses due to the presence in its genome of the genetic determinant of any of the paragraphs 1-10.

18. Plant of paragraph 16, or seed of paragraph 17, wherein the virus is of the family Potyviridae, Bromoviridae, and/or of the family Virgaviridae.

19. Plant of paragraph 16 or 18, or seed of paragraph 17 or 18, which is a plant or a seed of a species selected from the group consisting of *Phaseolus vulgaris, Beta vulgaris, Brassica oleracea, Daucus carota, Lactuca sativa, Cucumis melo, Cucumis sativus, Cucumis pepo, Spinacia oleracea, Solanum lycopersicum, Capsicum annuum*, and *Citrullus lanatus*.

20. Plant of paragraph 16, 18, or 19 which is a *Cucumis sativus* plant comprising the genetic determinant of paragraph 9 or 10, wherein the genetic determinant comprises at least two copies, preferably at least three copies of the combination, which *Cucumis sativus* plant is resistant against Cucumber Green Mottle Mosaic Virus, and is optionally resistant against Cucumber Vein Yellowing Virus.

21. *Cucumis sativus* plant of paragraph 20 comprising the genetic determinant of paragraph 10 which plant is resistant against Cucumber Green Mottle Mosaic Virus and Cucumber Vein Yellowing Virus due to the presence of the genetic determinant.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for producing a *Cucumis sativus* plant resistant to Cucumber Green Mottle Mosaic Virus comprising introducing at least two copies of a combination of two linked RNA-dependent RNA polymerase 1 (RDR1) genes that are inversely oriented into the genome of the plant,
   wherein the combination of two linked RDR1 genes comprises at least one RDR1 gene that is represented by SEQ ID NO: 1 or has a sequence identity of at least 90% thereof, and at least one RDR1 gene that is represented by SEQ ID NO: 3 or has a sequence identity of at least 90% thereof.

2. A method for producing a *Cucumis sativus* plant resistant to Cucumber Green Mottle Mosaic Virus comprising introducing at least two copies of a combination of two linked RNA-dependent RNA polymerase 1 (RDR1) genes that are inversely oriented into the genome of the plant,
   wherein the combination of two linked RDR1 genes comprises at least one RDR1 gene that is represented by SEQ ID NO: 3 or has a sequence identity of at least 90% thereof, and at least one RDR1 gene that is represented by SEQ ID NO: 5 or has a sequence identity of at least 90% thereof.

3. The method as claimed in claim 2,
   wherein the plant is resistant to Cucumber Green Mottle Mosaic Virus and Cucumber Vein Yellowing Virus.

4. The method as claimed in claim 1,
   wherein the plant is a *Cucumis sativus* plant comprising two copies of said combination, the presence of which leads to resistance to Cucumber Green Mottle Mosaic Virus.

5. The method as claimed in claim 2,
   wherein the plant comprises at least two copies of said combination, the presence of which leads to resistance to Cucumber Green Mottle Mosaic Virus resistance and to Cucumber Vein Yellowing Virus.

6. The method as claimed in claim 4,
   wherein the plant is a *Cucumis sativus* plant comprising at least three copies of said combination, the presence of which leads to resistance to Cucumber Green Mottle Mosaic Virus resistance.

7. The plant produced by the method of claim 1-4, or 6, wherein the plant is resistant to Cucumber Green Mottle Mosaic Virus.

8. A seed capable of growing into the plant of claim 7.

9. The method as claimed in claim 1 or 2,
   wherein at least one of the RDR1 genes in the combination has an indel upstream of the start codon, wherein the indel results in a sequence upstream of the ATG start codon as presented in SEQ ID NO: 5.

10. The method as claimed in claim 1 or 2,
   wherein the two linked RDR1 genes that are inversely oriented are not more than 3000 bp apart.

11. The method as claimed in claim 10,
   wherein copies of combinations of two RDR1 genes are not more than 6000 bp apart.

12. The method as claimed in claim 5,
   wherein the plant comprises at least three copies of said combination, the presence of which leads to resistance to Cucumber Green Mottle Mosaic Virus resistance and to Cucumber Vein Yellowing Virus.

13. The plant produced by the method of claim 2, 3 or 12, wherein the plant is resistant to Cucumber Green Mottle Mosaic Virus and Cucumber Vein Yellowing Virus.

14. The plant produced by the method of claim 10, wherein the plant is resistant to Cucumber Green Mottle Mosaic Virus.

15. The plant produced by the method of claim 11, wherein the plant is resistant to Cucumber Green Mottle Mosaic Virus.

16. The plant produced by the method of claim 9, wherein the plant is resistant to Cucumber Green Mottle Mosaic Virus and Cucumber Vein Yellowing Virus.

17. The plant produced by the method of claim 10, wherein the plant is resistant to Cucumber Green Mottle Mosaic Virus and Cucumber Vein Yellowing Virus.

18. The plant produced by the method of claim 11, wherein the plant is resistant to Cucumber Green Mottle Mosaic Virus and Cucumber Vein Yellowing Virus.

* * * * *

SEQUENCE LISTING

<160> NUMBER OF SEQ ID NOS: 5

<210> SEQ ID NO 1
<211> LENGTH: 6786
<212> TYPE: DNA
<213> ORGANISM: Cucumis sativus
<220> FEATURE:
<221> NAME/KEY: source
<222> LOCATION: 1..6786
<223> OTHER INFORMATION: /organism="Cucumis sativus"
     /mol_type="unassigned DNA"
<220> FEATURE:
<221> NAME/KEY: misc_feature
<222> LOCATION: 400..499
<223> OTHER INFORMATION: /note="n=a, t, c, or g"

<400> SEQUENCE: 1

```
aatactacaa caataattct tctcccaaac acatactatc ataatccttc ctccaaacac      60
atacaatcat aacactacca ttcatattcc ttcccccaaa taacacatat taccataaca     120
ctaccaataa taacccaaac cttaaacaca tattatcata acaccaagat tattataaca     180
ctaggattgc cataatcttt ccctcccaa atgcaccta agaattttgc catatttgca       240
aaattataaa tcaatgtgct atatttgtga taacatgttc tcaaaatgct acctactaca    300
acttttcaat aaataagtag agactaacta gagcaaggtc aggacaggga gtgtcttcat    360
cttggtttag ctcacagtga gttttaattt ttttttttn nnnnnnnnn nnnnnnnnn       420
nnnnnnnnn nnnnnnnnn nnnnnnnnn nnnnnnnnn nnnnnnnnn nnnnnnnnn          480
nnnnnnnnn nnnnnnnnc ttccactccc tctccattct ccacgtggtt cagtgcaggt      540
ctcgggcacc cgtctcactg gaaaaattgg acatgtctag aaatatttaa agcatatctc    600
aaagtttacg gtcattggta ttctctctat gaagaccttc aaaatattat ttaacacggt    660
cacaattaaa tatttgagag agaaacaacg taagtatttc aaaatatgta tcaataaatt    720
ttgtaggtat ttccatattt atgtagatta ttgtgaatca accttgtat catatgatta    780
aaaatatata tatgaaacaa caaaatgtac taatatgtaa atctaatata atataaacaa    840
tatggtatat tttctattga ttcctttaat aagaaaatgt tttctataat tttttttaaa    900
aaaatatcaa tccacataga aaattcatat ccattggcgg ctcattcaat aatttaatat    960
attcttttcg aaaactagaa gccaaaatta aaaaaaaaaa gaaattacat tcaatagaga   1020
atatttggtg ttatggccat ggaaagctca aaagaaaga cctgtcaatg aaagtctttc    1080
tttactctta agctaaaggc ccccaattat ggaattatat ctcttcattc ctccattttc    1140
gtttctccat tccccaactc tcctattttg cactacactg ttctctactg ccttctgcat   1200
cctctttttca tgaatcaatc tgcttggtat tcacctaact ttttcttcca ttgttgagaa   1260
tagatggact attgatgtgt ttttctttt atattgtaaa gctattcttc tttctttgtg    1320
tttcttcatc tgggttcatt ttttatcatg ttttttccca tttcttttg ttcccctgta    1380
ttttctttgt atttagcaac gtatcctctt ctgctctctc tgtagattct tactgcttct   1440
ggggctgttt atgatctggg gttgtttctt gtcttcaaat tttagttttc actatgtggg   1500
tgtccgtttg attatgaaaa cgtgttattc tgatgttccc acacattttc ttgatcatgt   1560
atgagttacc attagtatgc attctgctct ttaccaaatg agtataatgt gatctagctt   1620
tctctattaa tgtcggtgag atcctctata tcttgaatgt gtcataccttt tcaatttga   1680
tcaagatgat aatgtttttg catttggaat gaagttatat atagaaactt atggaaaaag  1740
ggttaaataa atattaatct ttcctcgatg gaatgtaaga aacactttttt aatctatctg  1800
```

```
ctcacttctt tattttgaga cttggttttt tgggttgaat aatatatggg gtgaggtatt    1860
tgaacagttg atcttttggt caagggtaca tatattatgc tagttgaact tggctttctt    1920
tttaggcttc atcatatgca ttgtaatcaa tttgtttgat atgacagaaa gaagttcgga    1980
gttgattttt cttggattgg atgggtaaaa caattcagct ttttggattc ccttctggtg    2040
tattgcaaga atcagttaag acgtttgtag agggaattac aggcacagga actattgatg    2100
ccataaatac gaaacgttcg aagggaggag gaagacgagt gtatgctatc atccagttta    2160
ctgatgaaga aggtgctaag tcaattatat ctaaggctac tgaacgcctt tgttatggta    2220
cttcttatct gaaggcaagg gagatgaaac atgatattct accagatccg cttgtctttg    2280
attacaactt caaagctcta agactacatc ttggctgtca gatatcaaag gaaagttttt    2340
ccgtgttatg gacagagtcg aatgtttctg tagatttcgg gtttgagctg cgcaagcttt    2400
atttcttcat atcctatcct cgtgttgact acatgctcgt attgcgctac gagaacattt    2460
ggcaggttga gttacacaag ccacatggtc aatctgtaga ttatcttctg attcaggttc    2520
atccattaac tttgaacaat gtcatgtcat tagtgtactg ttgtattttc tcctcactat    2580
tgagaaatat cattgattca tcccaagcaa gtttcaccta aattttcac tttattcatg    2640 gtattgttct ctaattacgg ggattcaact actgactcat gtacgtgctc ataggcctga    2700
tttccatcac agaacagtgg acggatataa aatgataact gaaataaaa atttagtgaa    2760 ccactaaaat catcatttat acctaagttc ctgagagaaa tatatagact gaacactta    2820 tgggacaaag gaattaagtg aatttattga taacttcgat gcaaaaaga actgagaaac    2880 gatcaaggtt ttatcaaaag attgtaaaag ggatagtgga agatagctgt agataaattc    2940
cagtgcttca aatgggtgaa agaagctata attttattaa aaaggtgtct tagttgataa    3000
ttttatcata cattttttct ccaacttgat aacttcaaga ctatgggtag gatttggata    3060
taatgagatt ttgagccata taaggttaat gttgtttagt aattgtaatc tggcaggata    3120
tgttttcttt gaacagagct aaaacatgtc cctagatatg aattttaaca agctaagtat    3180
aaacagaact aagcttgcaa cttttctata tttctatact tcaggataag cttataaacg    3240
caggtaatcc gtgcaagtga acatatgttt cataaaaaca aattatgctg tcttcatact    3300
gatgttgaaa taagcaagtc aaagttcaat ggcaaagaat ttgagaatag cttaggttct    3360
tggcccatgc acatttatg ttgtatatat tctaactatg acatgtttgt actgttagtt    3420
atttggtgct ccacggattt atgaaagaga tgcaaggtct tttggactca ttactgaaga    3480
ccctttctta aacttttcca cggaaattga cacccaatgg tttcgagcaa ctgattttac    3540
tccatcatgt agtattggac aatctgctgc tttatgcttg gagattccct acggtcgcca    3600
gctccctaat tttcatgata aatttgctta cttcaaagaa atcaagggta aatttacatt    3660
ggtcagtggt tctacttatt cctccaatgt aaacttggta cctgtagtta cacctcctcg    3720
aaccatcaac ttgccatata caattttgtt taagataaat ttgttggtac aacaaggatg    3780
tcttccaggc ccagctcttg atattagttt ctatcagatg gtagattctc agatatacaa    3840
tactgccgtc atagatcatg cgttaaagaa acttctccac ttgaaagagt gttgctataa    3900
cccttcaaaa tggttagatg aggaatacag aaagtacttc aaattaaaga atccccccca    3960
gccacctatt ttgaccttga atgaagggtt agtctatgta cacagggttc aagtgacacc    4020
ttgtaaagtt tacttttgtg gtccagaagt taacatttca aatcgtgtat tacgccggta    4080
tcctgactac attgacaact ttttgcgtgt ttcatttgtt gacgaggaat tgggtaaaat    4140
gtattcaact gagttgtctc cacgtgcatc ttcttctttg gaggatggaa agacaaaaat    4200
```

```
ttttaaacgg attctttcag ttctaagaga tggcatcact attggtgata agaagtttga    4260
gtttctagct tattcatcta gtcaattacg ggaaaatgct gcatggatgt ttgctccaaa    4320
aaatgaactt actgcagcta aaataaggca atggatggga gattttcata atatacgaaa    4380
tgtagccaag tatgctgcta gactaggcca atcctttggt tcatcaacag aaactttaag    4440
tgtcagtaga cgtgaagtta aagttattcc tgatattgaa gttgaatcag gtagtggtgt    4500
caattatgtc ttctctgatg gtattgggaa aatagcagct agttttgcta gaaaagtggc    4560
taaaaaatgt gggatcaggc atacaccatc tgcttttcag attcgttatg ctggttttaa    4620
aggtgttatt tctgttgatc ctacctcatc agtaaaatta tcgctaagga acagcatgct    4680
caagtatgaa tcaacagaca cgaagcttga tgttttatca tggagtaaat atcatccttg    4740
ctttctaaat cgtcagttga ttactctttt gtctacactt ggagttcagg atcatgtttt    4800
tgagagtaaa caacaggagt tgattgatga attggacacc attttagtg atccattgaa    4860
ggctcagcag gctcttgagc taatgtctcc aggagagaat accaagatac ttaaggaaat    4920
gatgttgtgc ggttacaaac ctgattctga acctttctta agaatgatgt tgcacacatt    4980
cagagaatca aagttgatgg aattgcgaat gaagtcaagg atcttcattc caaatggaag    5040
agcaatgatg ggatgtctcg acgaaacaag aaacttggaa tatggggagg tatttgtgca    5100
gtgttctgca catcagcagc tgcatgacga tcgcgtaatc tttaagagaa taaaatcgaa    5160
ccggcatttc attgtaactg aacagttgt agtggccaaa aacccctgct gcacccagg    5220
tgatgtgcgc gttttaacag ccgtggatgt accatcactg catcacatga tagattgtgt    5280
ggtttttcca caaaagggt caaggtaaat gatctatttt aacatcaaaa tttacatgtc    5340
cagttcaagt aaaataaaat atatttctcc ttttcagtct tagatatatg tttatactcg    5400
acttaatgaa ttcttaactg tgtggctaag catctctaat gtcatcatgt ttactagtaa    5460
ttttgcttat cttagaaact tcttttttt tacttgcctt gagggtgtc ataactctaa    5520
ttgatcttac ctacctttat tctctatatt tcgtactttc ttccttctca agttgataaa    5580
accgtttctc ttcatgcctc tagatagcca acacatcatc agtgaactaa agtaaaacta    5640
tgtgttgttt tcttctctgc ctgctgattg ttttttgtcat agcacttgtc ttgtttgatt    5700
cttgcatgtt gattgtttct gtcataacac ttctctttct atgtaagacc tcatccaaat    5760
gaatgctctg gaagcgatct agatggtgat atttacttcg tctgttggga ccctgatttg    5820
attccacctc aacaagttga accaatggat tataccctg tacctagcca agtactagat    5880
catgatgtca caatggaggt atggtttaca agtgaacttt gaactgttgt tatcatcaac    5940
aagtatttta gaggaaaaag gttgttctat agtgtaaatg ttgtaatgca ggaggtccag    6000
gagtatttg caattatat ggtcaatgac agtttaggaa tcattgccaa tgctcataca    6060
gcttttgcag ataaagagcc aaagaaagca atgagcaatc cttgtataca gctcgcaaaa    6120
ctattctcaa ttgcagtcga ctttccgaaa actggagtcc ctgctttaat acctgctaat    6180
ctaagagtaa aagaatatcc ggatttcatg gataaagccg acaaagtgac atacgagtcg    6240
gagaatgtac tggggaaact atttagaatg ttggatagca ttggtccaaa cattaagaat    6300
atcaggtcct tcaactatac gccggagatg gctcggcaag attatgaccc tgacatggaa    6360
gttgaaggtt tcgaggagta cctcgacgat gcaatatatc acaagaacaa ctatgacatg    6420
aggttgggaa atttgatgca ctatcataag atcaaaactg aggcggaatt gatcagtggt    6480
ggtagtttga cgtcatcatt atctttcacc atgaaaaatg aagcggaatc gattatcttg    6540
gctgtgaagt cgctgcgaaa ggaggcgagg ggctggttca atgagaaagc agacttacat    6600
```

```
tatggacatc atactaatgt gtatgcaaga gcttcagcat ggtattttgt tacatatcat    6660
cacacctact gggggtggtc tgatggcaga aagaatcatg gccatttttct tagctttcca   6720 tggtgtgttt atgataaact catccgtatc aagcaccgca aaattaattg tagagctcgc    6780
tattga                                                               6786
```

```
<210> SEQ ID NO 2
<211> LENGTH: 1115
<212> TYPE: PRT
<213> ORGANISM: Cucumis sativus

<400> SEQUENCE: 2
```

| Met | Gly | Lys | Thr | Ile | Gln | Leu | Phe | Gly | Phe | Pro | Ser | Gly | Val | Leu | Gln |
|---|---|---|---|---|---|---|---|---|---|---|---|---|---|---|---|
| 1 | | | | 5 | | | | | 10 | | | | | 15 | |

| Glu | Ser | Val | Lys | Thr | Phe | Val | Glu | Gly | Ile | Thr | Gly | Thr | Gly | Thr | Ile |
| | | | 20 | | | | | 25 | | | | | 30 | | |

| Asp | Ala | Ile | Asn | Thr | Lys | Arg | Ser | Lys | Gly | Gly | Gly | Arg | Arg | Val | Tyr |
| | | | 35 | | | | | 40 | | | | | 45 | | |

| Ala | Ile | Ile | Gln | Phe | Thr | Asp | Glu | Glu | Gly | Ala | Lys | Ser | Ile | Ile | Ser |
| 50 | | | | | 55 | | | | | 60 | | | | | |

| Lys | Ala | Thr | Glu | Arg | Leu | Cys | Tyr | Gly | Thr | Ser | Tyr | Leu | Lys | Ala | Arg |
| 65 | | | | | 70 | | | | | 75 | | | | | 80 |

| Glu | Met | Lys | His | Asp | Ile | Leu | Pro | Asp | Pro | Leu | Val | Phe | Asp | Tyr | Asn |
| | | | | 85 | | | | | 90 | | | | | 95 | |

| Phe | Lys | Ala | Leu | Arg | Leu | His | Leu | Gly | Cys | Gln | Ile | Ser | Lys | Glu | Ser |
| | | | 100 | | | | | 105 | | | | | 110 | | |

| Phe | Ser | Val | Leu | Trp | Thr | Glu | Ser | Asn | Val | Ser | Val | Asp | Phe | Gly | Phe |
| | | | 115 | | | | | 120 | | | | | 125 | | |

| Glu | Leu | Arg | Lys | Leu | Tyr | Phe | Phe | Ile | Ser | Tyr | Pro | Arg | Val | Asp | Tyr |
| | | 130 | | | | | 135 | | | | | 140 | | | |

| Met | Leu | Val | Leu | Arg | Tyr | Glu | Asn | Ile | Trp | Gln | Val | Glu | Leu | His | Lys |
| 145 | | | | | 150 | | | | | 155 | | | | | 160 |

| Pro | His | Gly | Gln | Ser | Val | Asp | Tyr | Leu | Leu | Ile | Gln | Leu | Phe | Gly | Ala |
| | | | | 165 | | | | | 170 | | | | | 175 | |

| Pro | Arg | Ile | Tyr | Glu | Arg | Asp | Ala | Arg | Ser | Phe | Gly | Leu | Ile | Thr | Glu |
| | | | 180 | | | | | 185 | | | | | 190 | | |

| Asp | Pro | Phe | Leu | Asn | Phe | Ser | Thr | Glu | Ile | Asp | Thr | Gln | Trp | Phe | Arg |
| | | 195 | | | | | 200 | | | | | 205 | | | |

| Ala | Thr | Asp | Phe | Thr | Pro | Ser | Cys | Ser | Ile | Gly | Gln | Ser | Ala | Ala | Leu |
| | 210 | | | | | 215 | | | | | 220 | | | | |

| Cys | Leu | Glu | Ile | Pro | Tyr | Gly | Arg | Gln | Leu | Pro | Asn | Phe | His | Asp | Lys |
| 225 | | | | | 230 | | | | | 235 | | | | | 240 |

| Phe | Ala | Tyr | Phe | Lys | Glu | Ile | Lys | Gly | Lys | Phe | Thr | Leu | Val | Ser | Gly |
| | | | | 245 | | | | | 250 | | | | | 255 | |

| Ser | Thr | Tyr | Ser | Ser | Asn | Val | Asn | Leu | Val | Pro | Val | Thr | Pro | Pro |
| | | | 260 | | | | | 265 | | | | | 270 | |

| Arg | Thr | Ile | Asn | Leu | Pro | Tyr | Thr | Ile | Leu | Phe | Lys | Ile | Asn | Leu | Leu |
| | | | 275 | | | | | 280 | | | | | 285 | | |

| Val | Gln | Gln | Gly | Cys | Leu | Pro | Gly | Pro | Ala | Leu | Asp | Ile | Ser | Phe | Tyr |
| | | 290 | | | | | 295 | | | | | 300 | | | |

| Gln | Met | Val | Asp | Ser | Gln | Ile | Tyr | Asn | Thr | Ala | Val | Ile | Asp | His | Ala |
| 305 | | | | | 310 | | | | | 315 | | | | | 320 |

| Leu | Lys | Lys | Leu | Leu | His | Leu | Lys | Glu | Cys | Cys | Tyr | Asn | Pro | Ser | Lys |
| | | | | 325 | | | | | 330 | | | | | 335 | |

-continued

```
Trp Leu Asp Glu Glu Tyr Arg Lys Tyr Phe Lys Leu Lys Asn Pro Pro
            340                 345                 350

Gln Pro Pro Ile Leu Thr Leu Asn Glu Gly Leu Val Tyr Val His Arg
        355                 360                 365

Val Gln Val Thr Pro Cys Lys Val Tyr Phe Cys Gly Pro Glu Val Asn
    370                 375                 380

Ile Ser Asn Arg Val Leu Arg Arg Tyr Pro Asp Tyr Ile Asp Asn Phe
385                 390                 395                 400

Leu Arg Val Ser Phe Val Asp Glu Glu Leu Gly Lys Met Tyr Ser Thr
                405                 410                 415

Glu Leu Ser Pro Arg Ala Ser Ser Leu Glu Asp Gly Lys Thr Lys
            420                 425                 430

Ile Phe Lys Arg Ile Leu Ser Val Leu Arg Asp Gly Ile Thr Ile Gly
        435                 440                 445

Asp Lys Lys Phe Glu Phe Leu Ala Tyr Ser Ser Gln Leu Arg Glu
        450                 455                 460

Asn Ala Ala Trp Met Phe Ala Pro Lys Asn Glu Leu Thr Ala Ala Lys
465                 470                 475                 480

Ile Arg Gln Trp Met Gly Asp Phe His Asn Ile Arg Asn Val Ala Lys
                485                 490                 495

Tyr Ala Ala Arg Leu Gly Gln Ser Phe Gly Ser Ser Thr Glu Thr Leu
            500                 505                 510

Ser Val Ser Arg Arg Glu Val Lys Val Ile Pro Asp Ile Glu Val Glu
        515                 520                 525

Ser Gly Ser Gly Val Asn Tyr Val Phe Ser Asp Gly Ile Gly Lys Ile
    530                 535                 540

Ala Ala Ser Phe Ala Arg Lys Val Ala Lys Lys Cys Gly Ile Arg His
545                 550                 555                 560

Thr Pro Ser Ala Phe Gln Ile Arg Tyr Ala Gly Phe Lys Gly Val Ile
                565                 570                 575

Ser Val Asp Pro Thr Ser Ser Val Lys Leu Ser Leu Arg Asn Ser Met
            580                 585                 590

Leu Lys Tyr Glu Ser Thr Asp Thr Lys Leu Asp Val Leu Ser Trp Ser
        595                 600                 605

Lys Tyr His Pro Cys Phe Leu Asn Arg Gln Leu Ile Thr Leu Leu Ser
    610                 615                 620

Thr Leu Gly Val Gln Asp His Val Phe Glu Ser Lys Gln Gln Glu Leu
625                 630                 635                 640

Ile Asp Glu Leu Asp Thr Ile Phe Ser Asp Pro Leu Lys Ala Gln Gln
                645                 650                 655

Ala Leu Glu Leu Met Ser Pro Gly Glu Asn Thr Lys Ile Leu Lys Glu
            660                 665                 670

Met Met Leu Cys Gly Tyr Lys Pro Asp Ser Glu Pro Phe Leu Arg Met
        675                 680                 685

Met Leu His Thr Phe Arg Glu Ser Lys Leu Met Glu Leu Arg Met Lys
    690                 695                 700

Ser Arg Ile Phe Ile Pro Asn Gly Arg Ala Met Met Gly Cys Leu Asp
705                 710                 715                 720

Glu Thr Arg Asn Leu Glu Tyr Gly Glu Val Phe Val Gln Cys Ser Ala
                725                 730                 735

His Gln Gln Leu His Asp Asp Arg Val Ile Phe Lys Arg Ile Lys Ser
            740                 745                 750
```

```
Asn Arg His Phe Ile Val Thr Gly Thr Val Val Ala Lys Asn Pro
        755                 760                 765

Cys Leu His Pro Gly Asp Val Arg Val Leu Thr Ala Val Asp Val Pro
    770                 775                 780

Ser Leu His His Met Ile Asp Cys Val Val Phe Pro Gln Lys Gly Ser
785                 790                 795                 800

Arg Pro His Pro Asn Glu Cys Ser Gly Ser Asp Leu Asp Gly Asp Ile
                805                 810                 815

Tyr Phe Val Cys Trp Asp Pro Asp Leu Ile Pro Pro Gln Gln Val Glu
                820                 825                 830

Pro Met Asp Tyr Thr Pro Val Pro Ser Gln Val Leu His Asp Val
        835                 840                 845

Thr Met Glu Glu Val Gln Glu Tyr Phe Ala Asn Tyr Met Val Asn Asp
        850                 855                 860

Ser Leu Gly Ile Ile Ala Asn Ala His Thr Ala Phe Ala Asp Lys Glu
865                 870                 875                 880

Pro Lys Lys Ala Met Ser Asn Pro Cys Ile Gln Leu Ala Lys Leu Phe
                885                 890                 895

Ser Ile Ala Val Asp Phe Pro Lys Thr Gly Val Pro Ala Leu Ile Pro
                900                 905                 910

Ala Asn Leu Arg Val Lys Glu Tyr Pro Asp Phe Met Asp Lys Ala Asp
                915                 920                 925

Lys Val Thr Tyr Glu Ser Glu Asn Val Leu Gly Lys Leu Phe Arg Met
            930                 935                 940

Leu Asp Ser Ile Gly Pro Asn Ile Lys Asn Ile Arg Ser Phe Asn Tyr
945                 950                 955                 960

Thr Pro Glu Met Ala Arg Gln Asp Tyr Asp Pro Asp Met Glu Val Glu
                965                 970                 975

Gly Phe Glu Glu Tyr Leu Asp Asp Ala Ile Tyr His Lys Asn Asn Tyr
                980                 985                 990

Asp Met Arg Leu Gly Asn Leu Met His Tyr His Lys Ile Lys Thr Glu
                995                 1000                1005

Ala Glu Leu Ile Ser Gly Gly Ser Leu Thr Ser Ser Leu Ser Phe Thr
    1010                1015                1020

Met Lys Asn Glu Ala Glu Ser Ile Ile Leu Ala Val Lys Ser Leu Arg
1025                1030                1035                1040

Lys Glu Ala Arg Gly Trp Phe Asn Glu Lys Ala Asp Leu His Tyr Gly
                1045                1050                1055

His His Thr Asn Val Tyr Ala Arg Ala Ser Ala Trp Tyr Phe Val Thr
                1060                1065                1070

Tyr His His Thr Tyr Trp Gly Trp Ser Asp Gly Arg Lys Asn His Gly
                1075                1080                1085

His Phe Leu Ser Phe Pro Trp Cys Val Tyr Asp Lys Leu Ile Arg Ile
                1090                1095                1100

Lys His Arg Lys Ile Asn Cys Arg Ala Arg Tyr
1105                1110                1115

<210> SEQ ID NO 3
<211> LENGTH: 8001
<212> TYPE: DNA
<213> ORGANISM: Cucumis sativus
```

```
<220> FEATURE:
<221> NAME/KEY: source
<222> LOCATION: 1..8001
<223> OTHER INFORMATION: /organism="Cucumis sativus"
      /mol_type="unassigned DNA"

<400> SEQUENCE: 3
ttaaatcacg ttttaaaaa tgaaaactac catatcaagc attagtatgg tcaataagtg      60
ggtgtttgtt gaactataat aaagtatgat tgtaatataa tataatctaa aatccatgtt    120
tggataccgt atttgcgttc aaattgcaat atcgaactta ttttgtttat gcaaatttta    180
gtttaatatt gttagaata gttgtaaata taacaaataa atttaaaata attaagaata     240
taacaacatt tttaaaaaat tgcaaatata acaaaatctg taaagtcta tcaataatag     300 attatgttgc aaatattggt ctatcactaa taaatcataa gagtctagtg tagactttgc    360
aatatttaca atgtttttaa aatgctgtta tatacttaat tattatttct aaaactgtta    420
tccattataa ttactcatct agtttctttt tcatcgtttt cacggttcaa gatcctattt    480
ttatttggtt ctcaatcgtt gtgcattcca gcactcctct tgttaccaat aatctatttt    540
ggctttccaa acaaccgata aggatcaatg taaatagtta aaagacttag ataaatagat    600
tcaagttagt gttgtgttta tttgagtttc tcaacaaaat attgaatagt tactgtagtt    660
agttgggcac tcttagtctt atatcttgaa aatataagaa aattacgtgg ttttgagaga    720
aatattgcat attttttatt attgaatatg acccaataat aggtaaaaat actaccgaag    780
aaattctatc caaggtaact tatggttcct ttggattagc tttaactaca agtcttggta    840
aaaatgaatg agtttctctt gtacctcttt aaaaacaaca acgtaacaca aaatatactg    900
ctaaacataa aagtaaagtc aaagatgaat atgacgagag ttataacaat taatattata    960 gaataaaat tattatatga aatgaaaaac acatacctt tcaaagaag gaaaaacaca       1020 tccaacgagt aaaagaata aaagtaacct aaatggagga aaaattaaaa tgttcgtaaa    1080
aacatggttg aaggaaagtt tgaaaagaag ataaaatgtt accaactaaa ctaatgtgtt    1140
aggaaagaag taagaatttg aaaagataat gaagcaaatt aattataaaa taatgtaatt    1200
aataaattcc ttttacaaaa gtctacttag ttatttactt taatataaa caatatgtaa     1260 tgcttatttg gcaaagaata atagaattga agagaaaagg attattgttg taaattaatg    1320
tgaattgaat aatattattt gaaaagtgag aattcatata attggtttgt gttttttatta    1380 agaaatagaa aaagagaaaa taattgtact agaaaggtta aacttaggta gcaagttttg    1440
tttgtgattt tcccatctgg cgtcaagtca aggcttttgg gaaatgaagt ctattattaa    1500
agctttcaag ttcttctcat gccccacaaa aacattttta agaatattac tttacttgaa    1560
attaattatt tttacttatt cttacttttc agtacgcttt atctttaatg taatcatata    1620
atagaaacac actaaaattt aattagcatc aataagtaaa tttgaaaatc aaggaaacat    1680
aaaacctaaa ataagggaa ccccatgttg aaattttgtg cattaaatag caaaaatttg     1740
acttttgatc cacagcctta tttggtgaat tactccatga tgtttgatt ttgatttaga     1800 ccatattggt aaaacatatt ctaagtcctt cttttagctc tcccacaacg tcccttatt     1860 tatgatgtt cattatttca gtcatagtgt gccaacttct ttcggtcact aggtctatcc     1920
gtagaagata aagtttcaac cgatcattta agaaaacga gtagatattg ttatagatta    1980
aaatcaaaaa gattgatgaa attggattgg aatctatatt tgttgattg attttttgtca    2040 acaaattaat ctatatttat atgagtgaga tgaaggaaa tgaagaatta aagaaaaga     2100 cattggagat attttaaatt tattaaggta tgttcatata tttggttgg atttggtttg    2160
```

```
gggatggatt ttcagacaaa gatcaaacaa attaaaaaat ggttgatttt ctccaaattc    2220
aatccaattc attgggtaag tttggtttga tttggtttta cccattttga aaccacaagg    2280
actaaatatg atccatcaaa tttggtgaca gaaatatgtt tttgtattaa aaatggtgat    2340
ttcacaagaa aaaccaaga aaaatagagc aagatgaaaa ggttaaccaa agggtgctat    2400 ttcttttga caatttgact ggttacacct cacttgatca gtctctactt cacgatccct    2460
cgtctccctc tgtatgggct ctcaaacggt cagaccaaaa gttacgttgg aattactggc    2520
gctgaagcga ttttcttctt tcaaagctcc aacagtatgt tctgttcatc actccttctc    2580
cttttgcttt ccttttcttc tgggtttatg gccttttgat gttgcttcag ttttttgacat    2640 tccattaaac ctcttcttgt aattaccaac taactgggga ctgggcttgc tgctcttgca    2700
gttgactctt cgcattcctc tgttttact ctgtttttac actgtttttt ggttttgatt    2760
gctctactgg gttcatatgg aaacttcaaa atcctaaagt tttcatttcg gtttatcgat    2820
ttgtgccact tggaggggat ttttcatgtt tttttttttt ttaactgtgg gtttctctgt    2880
gtttcttctg ctcatatctt ttgtgccttt taattgtctt ttcttcccaa attcccttca    2940
agatcctcag gttttgtac ccagtggagg acatttatgt tttatgtgt gtgcgttgga    3000 ccttttttct tcttcatcat tacatcatgc tattttctc attttcttgg cgcttttgaa    3060
tttcttttct tgaattttt ttagttggag tttgatctag gcgagcactc aggttggaaa    3120
ctcgagcatt cacctatatt ctgggctgt ctgattgtgt gtctcttccc attttcaaaa    3180
caaaggtttc tttggtttct tttcattgag tgtttcttgt cgagtaggtt actcttcttt    3240
tcttcatttc atttaactta tctgcatctg aattgtcact gattctaatt caatccatgt    3300 attggtatt gtttctcttc gtaggacaac attcacccctt ggcagtttca ttaactagac    3360
cttattttct tcacattgtc atggaatgct ccattcaaat tggaacccca atacgcatag    3420
gagcatagaa gttaggcctc ttagaaagtc gtgaaagatt tctttggaat ctcatgggga    3480
aaacaattca cattagtgga tttccttcac atgtcaccgc agatgctgtt aagaattttt    3540
tggagggtca tacaggtcca ggtactgtgt atgccataaa ggttagacca cctaagagag    3600
ggggaggtag actatatgct attgttcaat tcactagtgc tacacaagct gagttgatca    3660 tttcttttagc taatcaacgt ctatggtacg atcttcctta tcttaaggct cgggcaaccg    3720
aggttgatat tgtaccaaaa cctaggacat acatgtatac cttggaagag ttgctgctat    3780
gctttggttg tcaagtctca actgaaaagt ttcgtgttct atgggaagga aatgttgatt    3840
tggtgacttt tggaattgga atgcggaaaa tgaactttca tttgaaatat aagtctgttg    3900
agtataggct tgagctttca tatgagatca tttggcagat acaactgcac tgtccgcgag    3960
atcagtctat gaagtatctt ctgatccagg ttctatgatc aaatgtctat ctaaattgt    4020 ttcatttat tttgaaaagc ataattatcc tctcttgtaa agttgaaaca ttttgctata    4080
cttgtttaaa ttgtttcaac tattgtgtta gttgtttgaa cattaaatcg atgtaacctt    4140
gttgaaaatg ttgctatttg tcttaaatag tagatatgtt actcacatgt aagcttaata    4200
gtcaggttat cttttttcatg ttttttcttat cagttaagtg gagctcctcg gatatataaa    4260
aaagttgcac cgaatagtgg acaaatcttc gacaatccac ttttgaactt ttttaaggaa    4320
gcatctgatg atcaatgggt tagaacgact gattttactt catcatgctc tattggacaa    4380
tcttcttctt tatgtttgaa gctacctaat ggccgtcaac ttccaccttt taaacaaaat    4440
tttgcttatt atgaagaatt tgaacatgaa ttccgcttga tagatgaaga tgccaatttt    4500 tcttttttgta gagatcttgc tcccattgtt gattctcgtt ctcatgttct gccgtataaa    4560
```

```
attttgttta aaataaatgc attagttcaa tatggttgca ttccatggcc attacttgat    4620
gctagtttct accggttggt cgaaagaata ataacaacaa gaattgaatt tgttgaacat    4680
gccttggaaa aactgttcca tttaaaggaa tgcaactatg atccatcaaa ctttcttaca    4740
gagcagtaca gaaagtattc aagacatcct ccaaattctc ctgttatatc cttggatgat    4800
ggtttggtat atgttcgtag ggttcaaata acaccttgta aggtgttctt ctgtggtcct    4860
gaagtcaatg tctcaaatcg ggtgttgcgc cattttctc aatatattga taattttctt     4920
cgtgtgtctt ttgttgatga ggagtgggat aaaatgcgtt caacagattt attgccacgg    4980
atgtcttcaa agagtgagga tggtaaaact gatatctaca ggagaattct ctctgttctt    5040
aaaaatggca tagtcatagg tgataaaacc tttcagtttc ttgcattctc atcaagccaa    5100
ttaagagata attccttgtg gatgtttgct tccggacctg atattgacgc agcttatatt    5160
agagcgtgga tgggcgattt tcgacatatc aagaatcccg caaagtatgc tgctagattg    5220
gccaatcat tcggctcatc gacagaggca ctttcagttg ctagtaatga aagggaaatt     5280
attcctgaca tagaggttca acaggagaa atcaagtatg tcttttctga tggaattgga    5340
aaaatatcaa gcaaattcgc caaagaggtt gctgcaaaat gtggtttcca agccgtcccg    5400
tctgcttttc aaattcgtta tggtggatat aagggtgttg ttgctgttga tccgtactca    5460
actataaaat tatctctgag gaagagtatg tgcaaatttg aatcagacaa cacaaaactt    5520
gacgtcttag gccatagcaa ataccaacca tgcttcctta atcgtcaact gattactctc    5580
atgtctactc taggtgttag agacgaaatt tttgagaaaa acaaagtga agctgtagaa    5640
caattggatg ccatttaac agatccattg aaggctcaag aagctttgga gttgatgtct     5700
cccggagaga atactaatat tctcaaggaa atgctcaaat gtggctatca accagatgtc    5760
gagccgtatc tgtcaatgat gttacaaact ttccgggcat caagttgct agagttacgc     5820
accaaatcaa gaatctttat cccaaatggg agagcgatga tgggatgtct tgatgagacc    5880
aggaccttgg aatatgggca ggtatttgtg caaatctcca gtggtagaca tcgaaattta    5940
tctgaatcct tcgcattcaa tagaattggt cgagaacacc atttagttat tgaaggaaat    6000
gttacagttg ctaaaaatcc ctgcctgcac cctggtgatg ttcgtgtatt aaaggctgta    6060
aatatacctg gtttgtacca tatggttgac tgtgtagttt ttcctcaaaa aggatcaagg    6120
ttggtagtac attgaccaat gctagttctt tcttgatttg acaataagt tatgttttca     6180
aatttaaatg caagaaagcc ccttcacttc agaatagtaa catgtcaaca tatattttct    6240
agaataggtt ctgtgactaa tagcttgcat aattttggtt ggaagatttt cctcttaaat    6300
agatgttact aaccagattt tgtacttgtt tatttaggcc tcatccgaat gaatgctcag    6360
gtagtgattt agatggtgat atttacttg tctgttggga caccgaattg atcccgtctc     6420
gacaaattcc acctatggat tatactcctg cacctccaaa tgagttagat cgtgatgtta    6480
caactgaggt attttgacag tggcatgttt tgaaaacttg ataactcatg ccacttttc     6540
agtgtttaat ctccgtttta atatttgaca taacagtgaa cttcaattta tgttttttt    6600
cttaaaatag attcacgttg cgcattgctt ctcattagaa gagagaccat tcatgtttgt    6660
atgtgttctt agtcctaatc tgaaactact gttctttacc acaggatatc caagaatatt    6720
ttgtgaacta catggttaat gatagtcttg gaatcattgc caatgctcat actgcctttg    6780
cagataaaga gctcttttaaa gcaaggagta gtccttgttt ggagcttgca aagctattct    6840
ccgttgctgt ggacttccca aaaactggag taccagctat aataccttct catttatatg    6900
tcaaagagtt tcctgacttt atggagaagc ctgaccgacc ctcttatgaa tcaaacaaag    6960
```

-continued

```
taattggaaa acttttttcgg gctgtgaaag acattgcacc aactttaagc catattcggt    7020
catttactcg agatgtagca agaaggtgtt acgactgtga tatggaagtc gaaggctttg    7080
aagattatgt tgaagatgcc ttctatcata aaagcaatta tgattacaag ttggggaatt    7140
tgcttgatta ttatggtatc aagtctgagg cagaagtact tagtgggagt atcatgagga    7200
tgtccaagtc tttcaccagg agaagagatg cagaagcaat caacttggct gtaaggtctc    7260
tgagaaagga ggctaggaca tggttcaatg caagagaagg cgcagattcg aattcagatg    7320
atttatttgc caaagcttca gcttggtact atgttacata ccatcactct tattggggct    7380
gctataatga gggaatgaaa cgcgaccatt atttgagctt ccctggtgt gtttacgaca    7440
aactgatgca aatcaaggag aataatttga gaagaagaga gagagctgca agactggcaa    7500
gtttcgacag attcggacat gtgttaaatc ttggtgggag ttgaagaatg atcaatatgg    7560
ttggtttgct gtcagattga actaaatttt tctgtagctt taaatgattg aactaagaga    7620
ggaaacttga aatggaaatt gtcttttaac tcgttgaaaa cttgttagtt tataaggaat    7680
gttgtttctg tttaccgtgt aatatccaca ttcgcatgta cagagttcat gaaatctcaa    7740
accttagtct cactttctct taaactatag cccatcctcc tgccagcttt ttatgtgcgt    7800
actcgttgat ttatgagatc atctagtggg gaatctccat ctcgattcct ataaaattta    7860
acaaattttt ttttgtcaaa atgaatagtt aaacaaaagc aaggatgatg aagcctactt    7920
tgtctcctac cctgctctct aaacatctct atgtatcaat ggtcaacacc aggattatca    7980
gatatatcat atgttacaag a                                              8001
```

```
<210> SEQ ID NO 4
<211> LENGTH: 1130
<212> TYPE: PRT
<213> ORGANISM: Cucumis sativus

<400> SEQUENCE: 4

Met Gly Lys Thr Ile His Ile Ser Gly Phe Pro Ser His Val Thr Ala
1               5                   10                  15

Asp Ala Val Lys Asn Phe Leu Glu Gly His Thr Gly Pro Gly Thr Val
            20                  25                  30

Tyr Ala Ile Lys Val Arg Pro Pro Lys Arg Gly Gly Gly Arg Leu Tyr
        35                  40                  45

Ala Ile Val Gln Phe Thr Ser Ala Thr Gln Ala Glu Leu Ile Ile Ser
    50                  55                  60

Leu Ala Asn Gln Arg Leu Trp Tyr Gly Ser Ser Tyr Leu Lys Ala Arg
65                  70                  75                  80

Ala Thr Glu Val Asp Ile Val Pro Lys Pro Arg Thr Tyr Met Tyr Thr
                85                  90                  95

Leu Glu Glu Leu Leu Cys Phe Gly Cys Gln Val Ser Thr Glu Lys
            100                 105                 110

Phe Arg Val Leu Trp Glu Gly Asn Val Asp Leu Val Thr Phe Gly Ile
        115                 120                 125

Gly Met Arg Lys Met Asn Phe His Leu Lys Tyr Lys Ser Val Glu Tyr
    130                 135                 140

Arg Leu Glu Leu Ser Tyr Glu Ile Ile Trp Gln Ile Gln Leu His Cys
145                 150                 155                 160

Pro Arg Asp Gln Ser Met Lys Tyr Leu Leu Ile Gln Leu Ser Gly Ala
                165                 170                 175

Pro Arg Ile Tyr Lys Lys Val Ala Pro Asn Ser Gly Gln Ile Phe Asp
            180                 185                 190
```

-continued

```
Asn Pro Leu Leu Asn Phe Phe Lys Glu Ala Ser Asp Gln Trp Val
        195                 200                 205

Arg Thr Thr Asp Phe Thr Ser Ser Cys Ser Ile Gly Gln Ser Ser Ser
210                 215                 220

Leu Cys Leu Lys Leu Pro Asn Gly Arg Gln Leu Pro Pro Phe Lys Gln
225                 230                 235                 240

Asn Phe Ala Tyr Tyr Glu Glu Phe Glu His Glu Phe Arg Leu Ile Asp
                245                 250                 255

Glu Asp Ala Asn Phe Ser Phe Cys Arg Asp Leu Ala Pro Ile Val Asp
                260                 265                 270

Ser Arg Ser His Val Leu Pro Tyr Lys Ile Leu Phe Lys Ile Asn Ala
        275                 280                 285

Leu Val Gln Tyr Gly Cys Ile Pro Trp Pro Leu Leu Asp Ala Ser Phe
    290                 295                 300

Tyr Arg Leu Val Glu Arg Ile Ile Thr Thr Arg Ile Glu Phe Val Glu
305                 310                 315                 320

His Ala Leu Glu Lys Leu Phe His Leu Lys Glu Cys Asn Tyr Asp Pro
                325                 330                 335

Ser Asn Phe Leu Thr Glu Gln Tyr Arg Lys Tyr Ser Arg His Pro Pro
                340                 345                 350

Asn Ser Pro Val Ile Ser Leu Asp Asp Gly Leu Val Tyr Val Arg Arg
        355                 360                 365

Val Gln Ile Thr Pro Cys Lys Val Phe Phe Cys Gly Pro Glu Val Asn
    370                 375                 380

Val Ser Asn Arg Val Leu Arg His Phe Ser Gln Tyr Ile Asp Asn Phe
385                 390                 395                 400

Leu Arg Val Ser Phe Val Asp Glu Glu Trp Asp Lys Met Arg Ser Thr
                405                 410                 415

Asp Leu Leu Pro Arg Met Ser Ser Lys Ser Glu Asp Gly Lys Thr Asp
                420                 425                 430

Ile Tyr Arg Arg Ile Leu Ser Val Leu Lys Asn Gly Ile Val Ile Gly
        435                 440                 445

Asp Lys Thr Phe Gln Phe Leu Ala Phe Ser Ser Gln Leu Arg Asp
    450                 455                 460

Asn Ser Leu Trp Met Phe Ala Ser Gly Pro Asp Ile Asp Ala Ala Tyr
465                 470                 475                 480

Ile Arg Ala Trp Met Gly Asp Phe Arg His Ile Lys Asn Pro Ala Lys
                485                 490                 495

Tyr Ala Ala Arg Leu Gly Gln Ser Phe Gly Ser Ser Thr Glu Ala Leu
                500                 505                 510

Ser Val Ala Ser Asn Glu Arg Glu Ile Ile Pro Asp Ile Glu Val Gln
        515                 520                 525

Gln Gly Glu Ile Lys Tyr Val Phe Ser Asp Gly Ile Gly Lys Ile Ser
    530                 535                 540

Ser Lys Phe Ala Lys Glu Val Ala Ala Lys Cys Gly Phe Gln Ala Val
545                 550                 555                 560

Pro Ser Ala Phe Gln Ile Arg Tyr Gly Gly Tyr Lys Gly Val Val Ala
                565                 570                 575

Val Asp Pro Tyr Ser Thr Ile Lys Leu Ser Leu Arg Lys Ser Met Cys
                580                 585                 590

Lys Phe Glu Ser Asp Asn Thr Lys Leu Asp Val Leu Gly His Ser Lys
        595                 600                 605
```

-continued

Tyr Gln Pro Cys Phe Leu Asn Arg Gln Leu Ile Thr Leu Met Ser Thr
610                 615                 620

Leu Gly Val Arg Asp Glu Ile Phe Glu Lys Lys Gln Ser Glu Ala Val
625                 630                 635                 640

Glu Gln Leu Asp Ala Ile Leu Thr Asp Pro Leu Lys Ala Gln Glu Ala
            645                 650                 655

Leu Glu Leu Met Ser Pro Gly Glu Asn Thr Asn Ile Leu Lys Glu Met
            660                 665                 670

Leu Lys Cys Gly Tyr Gln Pro Asp Val Glu Pro Tyr Leu Ser Met Met
            675                 680                 685

Leu Gln Thr Phe Arg Ala Ser Lys Leu Leu Glu Leu Arg Thr Lys Ser
690                 695                 700

Arg Ile Phe Ile Pro Asn Gly Arg Ala Met Met Gly Cys Leu Asp Glu
705                 710                 715                 720

Thr Arg Thr Leu Glu Tyr Gly Gln Val Phe Val Gln Ile Ser Ser Gly
            725                 730                 735

Arg His Arg Asn Leu Ser Glu Ser Phe Ala Phe Asn Arg Ile Gly Arg
            740                 745                 750

Glu His His Leu Val Ile Glu Gly Asn Val Thr Val Ala Lys Asn Pro
            755                 760                 765

Cys Leu His Pro Gly Asp Val Arg Val Leu Lys Ala Val Asn Ile Pro
770                 775                 780

Gly Leu Tyr His Met Val Asp Cys Val Val Phe Pro Gln Lys Gly Ser
785                 790                 795                 800

Arg Pro His Pro Asn Glu Cys Ser Gly Ser Asp Leu Asp Gly Asp Ile
            805                 810                 815

Tyr Phe Val Cys Trp Asp Thr Glu Leu Ile Pro Ser Arg Gln Ile Pro
            820                 825                 830

Pro Met Asp Tyr Thr Pro Ala Pro Pro Asn Glu Leu Asp Arg Asp Val
            835                 840                 845

Thr Thr Glu Asp Ile Gln Glu Tyr Phe Val Asn Tyr Met Val Asn Asp
850                 855                 860

Ser Leu Gly Ile Ile Ala Asn Ala His Thr Ala Phe Ala Asp Lys Glu
865                 870                 875                 880

Leu Phe Lys Ala Arg Ser Ser Pro Cys Leu Glu Leu Ala Lys Leu Phe
            885                 890                 895

Ser Val Ala Val Asp Phe Pro Lys Thr Gly Val Pro Ala Ile Ile Pro
            900                 905                 910

Ser His Leu Tyr Val Lys Glu Phe Pro Asp Phe Met Glu Lys Pro Asp
            915                 920                 925

Arg Pro Ser Tyr Glu Ser Asn Lys Val Ile Gly Lys Leu Phe Arg Ala
930                 935                 940

Val Lys Asp Ile Ala Pro Thr Leu Ser His Ile Arg Ser Phe Thr Arg
945                 950                 955                 960

Asp Val Ala Arg Arg Cys Tyr Asp Cys Asp Met Glu Val Glu Gly Phe
            965                 970                 975

Glu Asp Tyr Val Glu Asp Ala Phe Tyr His Lys Ser Asn Tyr Asp Tyr
            980                 985                 990

Lys Leu Gly Asn Leu Leu Asp Tyr Tyr Gly Ile Lys Ser Glu Ala Glu
            995                 1000                1005

Val Leu Ser Gly Ser Ile Met Arg Met Ser Lys Ser Phe Thr Arg Arg
1010                1015                1020

Arg Asp Ala Glu Ala Ile Asn Leu Ala Val Arg Ser Leu Arg Lys Glu
1025                1030                1035                1040

Ala Arg Thr Trp Phe Asn Ala Arg Glu Gly Ala Asp Ser Asn Ser Asp
            1045                1050                1055

Asp Leu Phe Ala Lys Ala Ser Ala Trp Tyr Tyr Val Thr Tyr His His
        1060                1065                1070

Ser Tyr Trp Gly Cys Tyr Asn Glu Gly Met Lys Arg Asp His Tyr Leu
    1075                1080                1085

Ser Phe Pro Trp Cys Val Tyr Asp Lys Leu Met Gln Ile Lys Glu Asn
        1090                1095                1100

Asn Leu Arg Arg Arg Glu Arg Ala Ala Arg Leu Ala Ser Phe Asp Arg
1105                1110                1115                1120

Phe Gly His Val Leu Asn Leu Gly Gly Ser
            1125                1130

<210> SEQ ID NO 5
<211> LENGTH: 6745
<212> TYPE: DNA
<213> ORGANISM: Cucumis sativus
<220> FEATURE:
<221> NAME/KEY: source
<222> LOCATION: 1..6745
<223> OTHER INFORMATION: /organism="Cucumis sativus"
    /mol_type="unassigned DNA"
<220> FEATURE:
<221> NAME/KEY: misc_feature
<222> LOCATION: 400..499
<223> OTHER INFORMATION: /note="n = a, t, c, or g"

<400> SEQUENCE: 5
aatactacaa caataattct tctcccaaac acatactatc ataatccttc ctccaaacac     60
atacaatcat aacactacca ttcatattcc ttcccccaaa taacacatat taccataaca    120
ctaccaataa taacccaaac cttaaacaca tattatcata acaccaagat tattataaca    180
ctaggattgc cataatcttt ccctcccccaa atgcaccctc agaattttgc catatttgca    240
aaattataaa tcaatgtgct atatttgtga taacatgttc tcaaaatgct acctactaca    300
acttttcaat aaataagtag agactaacta gagcaaggtc aggacaggga gtgtcttcat    360
cttggtttag ctcacagtga gttttaattt ttttttttn nnnnnnnnn nnnnnnnnnn    420 nnnnnnnnnn nnnnnnnnnn nnnnnnnnnn nnnnnnnnnn nnnnnnnnnn nnnnnnnnnn    480
nnnnnnnnnn nnnnnnnnnc ttccactccc tctccattct ccacgtggtt cagtgcaggt    540
ctcgggcacc cgtctcactg gaaaaattgg acatgtctag aaatatttaa agcatatctc    600
aaagtttacg gtcattggta ttctctctat gaagaccttc aaaatattat ttaacacggt    660
cacaattaaa tatttgagag agaaacaacg taagtatttc aaaatatgta tcaataaatt    720
ttgtaggtat ttccatattt atgtagatta ttgtgaatca acctttgtat catatgatta    780
aaaatatata tatgaaacaa caaaatgtac taatatgtaa atctaatata atataaacaa    840
tatggtatat tttctattga ttcctttaat aagaaaatgt tttctataat ttttttttaaa   900 aaaatatcaa tccacataga aaattcatat ccattggcgg ctcattcaat aatttaatat    960 attctttttcg aaaactagaa gccaaaatta aaaaaaaaa caggtctcaa aaagaaagac   1020
ctgtcaatga aagtctttct ttactcttaa gctaaaggcc cccaattatg gaattatatc   1080
tcttcattcc tccattttcg tttctccatt ccccaactct cctatttgc actacactgt   1140 tctctactgc cttctgcatc ctctttttcat gaatcaatct gcttggtatt cacctaactt   1200
tttcttccat tgttgagaat agatggacta ttgatgtgtt tttctttta tattgtaaag   1260

```
ctattcttct ttctttgtgt ttcttcatct gggttcattt tttatcatgt ttttccccat   1320
ttcttttgt tcccctgtat tttctttgta tttagcaacg tatcctcttc tgctctctct    1380
gtagattctt actgcttctg gggctgttta tgatctgggg ttgtttcttg tcttcaaatt   1440
ttagttttca ctatgtgggt gtccgtttga ttatgaaaac gtgttattct gatgttccca   1500
cacattttct tgatcatgta tgagttacca ttagtatgca ttctgctctt taccaaatga   1560
gtataatgtg atctagcttt ctctattaat gtcggtgaga tcctctatat cttgaatgtg   1620
tcataccttt tcaatttgat caagatgata atgtttttgc atttggaatg aagttatata   1680
tagaaactta tggaaaaagg gttaaataaa tattaatctt tcctcgatgg aatgtaagaa   1740
acactttta atctatctgc tcacttcttt attttgagac ttggtttttt gggttgaata    1800
atatatgggg tgaggtattt gaacagttga tcttttggtc aagggtacat atattatgct   1860
agttgaactt ggctttcttt ttaggcttca tcatatgcat tgtaatcaat ttgtttgata   1920
tgacagaaag aagttcggag ttgattttc ttggattgga tgggtaaaac aattcagctt    1980
tttggattcc cttctggtgt attgcaagaa tcagttaaga cgtttgtaga gggaattaca   2040
ggcacaggaa ctattgatgc cataaatacg aaacgttcga agggaggagg aagacgagtg   2100
tatgctatca tccagtttac tgatgaagaa ggtgctaagt caattatatc taaggctact   2160
gaacgccttt gttatggtac ttcttatctg aaggcaaggg agatgaaaca tgatattcta   2220
ccagatccgc ttgtctttga ttacaacttc aaagctctaa gactcatctt tggctgtcag   2280
atatcaaagg aaagttttc cgtgttatgg acagagtcga atgtttctgt agatttcggg    2340
tttgagctgc gcaagcttta tttcttcata tcctatcctc gtgttgacta catgctcgta   2400
ttgcgctacg agaacatttg gcaggttgag ttacacaagc cacatggtca atctgtagat   2460
tatcttctga ttcaggttca tccattaact ttgaacaatg tcatgtcatt agtgtactgt   2520
tgtatttct cctcactatt gagaaatatc attgattcat cccaagcaag tttcacctaa    2580
atttttcact ttattcatgg tattgttctc taattacggg gattcaacta ctgactcatg   2640
tacgtgctca taggcctgat ttccatcaca gaacagtgga cggatataaa atgataactg   2700
aaaataaaaa tttagtgaac cactaaaatc atcatttata cctaagttcc tgagagaaat   2760
atatagactg aacactttat gggacaaagg aattaagtga atttattgat aacttcgatg   2820
caaaaaagaa ctgagaaacg atcaaggttt tatcaaaaga ttgtaaaagg atagtggaa    2880
gatagctgta gataaattcc agtgcttcaa atgggtgaaa gaagctataa ttttattaaa   2940
aaggtgtctt agttgataat tttatcatac attttttctc caacttgata acttcaagac   3000
tatgggtagg atttggatat aatgagattt tgagccatat aaggttaatg ttgtttagta   3060
attgtaatct ggcaggatat gttttctttg aacagagcta aaacatgtcc ctagatatga   3120
attttaacaa gctaagtata aacagaacta agcttgcaac ttttctatat ttctatactt   3180
caggataagc ttataaacgc aggtaatccg tgcaagtgaa catatgtttc ataaaaacaa   3240
attatgctgt cttcatactg atgttgaaat aagcaagtca aagttcaatg gcaaagaatt   3300
tgagaatagc ttaggttctt ggcccatgca cattttatgt tgtatatatt ctaactatga   3360
catgtttgta ctgttagtta tttggtgctc cacggattta tgaaagagat gcaaggtctt   3420
ttggactcat tactgaagac cctttcttaa acttttccac ggaaattgac acccaatggt   3480
ttcgagcaac tgattttact ccatcatgta gtattggaca atctgctgct ttatgcttgg   3540
agattcccta cggtcgccag ctccctaatt ttcatgataa atttgcttac ttcaaagaaa   3600
tcaagggtaa atttacattg gtcagtggtt ctacttattc ctccaatgta aacttggtac   3660
```

-continued

```
ctgtagttac acctcctcga accatcaact tgccatatac aattttgttt aagataaatt      3720
tgttggtaca acaaggatgt cttccaggcc cagctcttga tattagtttc tatcagatgg      3780
tagattctca gatatacaat actgccgtca tagatcatgc gttaaagaaa cttctccact      3840
tgaaagagtg ttgctataac ccttcaaaat ggttagatga ggaatacaga aagtacttca      3900
aattaaagaa tccccccag ccacctattt tgaccttgaa tgaagggtta gtctatgtac      3960
acagggttca agtgacacct tgtaaagttt acttttgtgg tccagaagtt aacatttcaa      4020
atcgtgtatt acgccggtat cctgactaca ttgacaactt tttgcgtgtt tcatttgttg      4080
acgaggaatt gggtaaaatg tattcaactg agttgtctcc acgtgcatct tcttcttttgg     4140
aggatggaaa gacaaaaatt tttaaacgga ttctttcagt tctaagagat ggcatcacta      4200
ttggtgataa aagtttgag tttctagctt attcatctag tcaattacgg aaaaatgctg       4260
catggatgtt tgctccaaaa atgaactta ctgcagctaa ataaggcaa tggatgggag        4320
atttcataa tatacgaaat gtagccaagt atgctgctag actaggccaa tcctttggtt       4380
catcaacaga aactttaagt gtcagtagac gtgaagttaa agttattcct gatattgaag      4440
ttgaatcagg tagtggtgtc aattatgtct ctctgatgg tattgggaaa atagcagcta      4500
gttttgctag aaaagtggct aaaaaatgtg ggatcaggca tacaccatct gcttttcaga      4560
ttcgttatgc tggttttaaa ggtgttattt ctgttgatcc tacctcatca gtaaaattat      4620
cgctaaggaa cagcatgctc aagtatgaat caacagacac gaagcttgat gttttatcat     4680
ggagtaaata tcatccttgc tttctaaatc gtcagttgat tactcttttg tctacacttg     4740
gagttcagga tcatgttttt gagagtaaac aacaggagtt gattgatgaa ttggacacca     4800
ttttagtga tccattgaag gctcagcagg ctcttgagct aatgtctcca ggagagaata     4860
ccaagatact taaggaaatg atgttgtgcg gttacaaacc tgattctgaa cctttcttaa    4920
gaatgatgtt gcacacattc agagaatcaa agttgatgga attgcgaatg aagtcaagga    4980
tcttcattcc aaatggaaga gcaatgatgg gatgtctcga cgaaacaaga aacttggaat    5040
atggggaggt atttgtgcag tgttctgcac atcagcagct gcatgacgat cgcgtaatct    5100
ttaagagaat aaaatcgaac cggcatttca ttgtaactgg aacagttgta gtggccaaaa    5160
accctgctt gcacccaggt gatgtgcgcg ttttaacagc cgtggatgta ccatcactgc      5220
atcacatgat agattgtgtg gtttttccac aaaagggtc aaggtaaatg atctattta      5280
acatcaaaat ttacatgtcc agttcaagta aaataaaata tatttctcct tttcagtctt     5340
agatatatgt ttatactcga cttaatgaat tcttaactgt gtggctaagc atctctaatg    5400
tcatcatgtt tactagtaat tttgcttatc ttagaaactt ctttttttt acttgccttg      5460
aggggtgtca taactctaat tgatcttacc taccttatt ctctatattt cgtactttct      5520
tccttctcaa gttgataaaa ccgtttctct tcatgcctct agatagccaa cacatcatca    5580
gtgaactaaa gtaaaactat gtgttgtttt cttctctgcc tgctgattgt ttttgtcata    5640
gcacttgtct tgtttgattc ttgcatgttg attgttctg tcataacact tctctttcta      5700
tgtaagacct catccaaatg aatgctctgg aagcgatcta gatggtgata tttacttcgt    5760
ctgttgggac cctgatttga ttccacctca acaagttgaa ccaatggatt ataccctgt      5820
acctagccaa gtactagatc atgatgtcac aatggaggta tggtttacaa gtgaacttg      5880
aactgttgtt atcatcaaca agtatttag aggaaaaagg ttgttctata gtgtaaatgt      5940
tgtaatgcag gaggtccagg agtattttgc aaattatatg gtcaatgaca gtttaggaat    6000
cattgccaat gctcatacag cttttgcaga taaagagcca aagaaagcaa tgagcaatcc    6060
```

-continued

```
ttgtatacag ctcgcaaaac tattctcaat tgcagtcgac tttccgaaaa ctggagtccc   6120
tgctttaata cctgctaatc taagagtaaa agaatatccg gatttcatgg ataaagccga   6180
caaagtgaca tacgagtcgg agaatgtact ggggaaacta tttagaatgt tggatagcat   6240
tggtccaaac attaagaata tcaggtcctt caactatacg ccggagatgg ctcggcaaga   6300
ttatgaccct gacatggaag ttgaaggttt cgaggagtac ctcgacgatg caatatatca   6360
caagaacaac tatgacatga ggttgggaaa tttgatgcac tatcataaga tcaaaactga   6420
ggcggaattg atcagtggtg gtagtttgac gtcatcatta tctttcacca tgaaaaatga   6480
agcggaatcg attatcttgg ctgtgaagtc gctgcgaaag gaggcgaggg gctggttcaa   6540
tgagaaagca gacttacatt atggacatca tactaatgtg tatgcaagag cttcagcatg   6600
gtattttgtt acatatcatc acacctactg gggtggtct gatggcagaa agaatcatgg   6660
ccattttctt agctttccat ggtgtgttta tgataaactc atccgtatca agcaccgcaa   6720
aattaattgt agagctcgct attga                                         6745
```